United States Patent [19]

Xu et al.

[11] Patent Number: 5,405,768
[45] Date of Patent: Apr. 11, 1995

[54] METHOD FOR CLONING AND PRODUCING THE AATII AND ALUI RESTRICTION ENDONUCLEASE AND METHYLASE AND RELATED METHOD FOR OVEREXPRESSING RESTRICTION ENDONUCLEASES

[75] Inventors: Shuang-yong Xu, Beverly; Donald O. Nwankwo, Peabody, both of Mass.

[73] Assignee: New England Biolabs, Inc., Beverly, Mass.

[21] Appl. No.: 134,570

[22] Filed: Oct. 8, 1993

Related U.S. Application Data

[63] Continuation-in-part of Ser. No. 909,947, Jul. 7, 1992, abandoned.

[51] Int. Cl.$^6$ ............................................. C12N 9/22
[52] U.S. Cl. ..................................... 435/199; 435/197; 435/320.1; 435/252.33; 536/23.2
[58] Field of Search ................. 435/194, 320.1, 252.33, 435/197; 536/23.2

[56] References Cited

U.S. PATENT DOCUMENTS 5,147,794  9/1992  Polisson et al. .................... 435/199

FOREIGN PATENT DOCUMENTS 0193413  9/1986  European Pat. Off. .
0437100A1  7/1991  European Pat. Off. .

OTHER PUBLICATIONS

K. D. Lunnen et al., Gene, 74:25-32 (1988).
Kosykh et al., Molec. Gen. Genet., 178:717-718 (1980).
Mann et al., Gene, 3:97-112 (1978).
Walder et al., Proc. Natl. Acad. Sci. USA, 78:1503-1507 (1981).
Bougueleret et al., Nucleic Acids Research, 12:3659-3676 (1984).
Gingeras et al., Proc. Natl. Acad. Sci. USA, 80:402-406 (1983).
Theriault et al., Gene, 19:355-359 (1982).
Blumenthal et al., J. Bacteriol., 164:501-509 (1985).
Szomolanyi et al., Gene, 10:219-225 (1980).
Janulaitis et al., Gene, 20:197-204 (1982).
Kiss et al., Gene, 21:111-119 (1983).
Walder et al., J. Biol. Chem., 258:1235-1241 (1983).
Raleigh et al., Proc. Natl. Acad. Sci. USA, 83:9070-9074 (1986).
Kiss et al., Nucleic Acid Research, 13:6403-6421 (1985).
Shine et al., Proc. Natl. Acad. Sci. USA, 71:1342-1346 (1974).
Sugisaki, et al., Nucleic Acids Research, 10:5747-5752 (1982).
Dubendorff, et al., J. Mol. Biol., 219:45-59 (1991).
Studier, J. Mol. Biol., 219:37-44 (1991).
Wang et al., Gene, 100:195-199 (1991).
Kues et al., Microbiological Reviews, 491-516 (1989).
Skoglund et al., Gene, 88:1-5 (1990).
Chatterjee et al., Nucl. Acids Res., 19(23):6505-6509 (1991).
Studier et al., J. Mol. Biol., 189:113-130 (1986).
Sato et al., Agric. Biol. Chem., 54(12):3319-3325 (1990).

*Primary Examiner*—Charles L. Patterson, Jr.
*Attorney, Agent, or Firm*—Gregory D. Williams; David G. Conlin; Peter F. Corless

[57] ABSTRACT

The present invention provides a novel approach to the production of restriction endonucleases. More specifically, there is provided a novel method for the overexpression of these enzymes, which comprises transforming a host cell with an expression vector containing DNA coding for the restriction endonuclease of interest and a vector for the expression of a methylase which is capable of protecting the host cell DNA against the restriction endonuclease of interest. The methylase vector is compatible with the restriction endonuclease expression vector. Preferably, the expression vector is a T7 expression vector and the cell is transformed with a third compatible vector which regulates the expression vector. Also disclosed is the cloning and overexpression of the AatII restriction endonuclease and methylase and the cloning and overexpression of the AluI restriction endonuclease and methylase.

5 Claims, 8 Drawing Sheets

```
    ATGACCGCTCGTCCGCAAGAAAAGCAAACAAAACGCAAATCAAATCAAAACTCATGGAAG
1   ---------+---------+---------+---------+---------+---------+   60
    TACTGGCGAGCAGGCGTTCTTTTCGTTTGTTTTGCGTTTAGTTTAGTTTTGAGTACCTTC
    MetThrAlaArgProGlnGluLysGlnThrLysArgLysSerAsnGlnAsnSerTrpLys

AGTAATTTAGAAGAAAGCATATCTTCAACGTGGGAAGATATTAGAGAAATTGGTGATCAG
61  ---------+---------+---------+---------+---------+---------+   120
    TCATTAAATCTTCTTTCGTATAGAAGTTGCACCCTTCTATAATCTCTTTAACCACTAGTC
    SerAsnLeuGluGluSerIleSerSerThrTrpGluAspIleArgGluIleGlyAspGln

CGGCGATCACATCTTTCAAATCGCACAACCTACGTTCTTGATGATGCAATTCATTTCTTA
121 ---------+---------+---------+---------+---------+---------+   180
    GCCGCTAGTGTAGAAAGTTTAGCGTGTTGGATGCAAGAACTACTACGTTAAGTAAAGAAT
    ArgArgSerHisLeuSerAsnArgThrThrTyrValLeuAspAspAlaIleHisPheLeu

TCAGAGCTTCCTCCAAACTCTATCCATGCTGTTGTTACCGATCCTCCGTATGGAGTCATT
181 ---------+---------+---------+---------+---------+---------+   240
    AGTCTCGAAGGAGGTTTGAGATAGGTACGACAACAATGGCTAGGAGGCATACCTCAGTAA
    SerGluLeuProProAsnSerIleHisAlaValValThrAspProProTyrGlyValIle

GAGTATGAAGACAAACACCACCAGAAATTGCGCTCTGGGCGGGGCGGGGTCTGGCGAATT
241 ---------+---------+---------+---------+---------+---------+   300
    CTCATACTTCTGTTTGTGGTGGTCTTTAACGCGAGACCCGCCCCGCCCCAGACCGCTTAA
    GluTyrGluAspLysHisHisGlnLysLeuArgSerGlyArgGlyGlyValTrpArgIle

CCTCCTTCATTTGACGGTGTGAAACGTAGCCCTCTCCCGCGCTTCACCGTGCTTTCTGAA
301 ---------+---------+---------+---------+---------+---------+   360
    GGAGGAAGTAAACTGCCACACTTTGCATCGGGAGAGGGCGCGAAGTGGCACGAAAGACTT
    ProProSerPheAspGlyValLysArgSerProLeuProArgPheThrValLeuSerGlu

GATGAATTAAACAGATTAAGCAGCTTTTTTTCTGCTTTAGCCTACGGTTTACACCGCGCC
361 ---------+---------+---------+---------+---------+---------+   420
    CTACTTAATTTGTCTAATTCGTCGAAAAAAAGACGAAATCGGATGCCAAATGTGGCGCGG
    AspGluLeuAsnArgLeuSerSerPhePheSerAlaLeuAlaTyrGlyLeuHisArgAla

CTTGTTCCTGGCGGCCATGTTTTCATGGCCGCCAACCCTTTGCTATCCTCAATGGTGTTC
421 ---------+---------+---------+---------+---------+---------+   480
    GAACAAGGACCGCCGGTACAAAAGTACCGGCGGTTGGGAAACGATAGGAGTTACCACAAG
    LeuValProGlyGlyHisValPheMetAlaAlaAsnProLeuLeuSerSerMetValPhe

CATGCTTTCCAGACCGCTGGTTTTGAGAAACGAGGTGAAGTTATTCGGTTAGTACAAACC
481 ---------+---------+---------+---------+---------+---------+   540
    GTACGAAAGGTCTGGCGACCAAAACTCTTTGCTCCACTTCAATAAGCCAATCATGTTTGG
    HisAlaPheGlnThrAlaGlyPheGluLysArgGlyGluValIleArgLeuValGlnThr

CTGCGCGGCGGTGACCGACCAAAAGGAGCAGAGAAAGAGTTTTCCGACGTCTCCATGATG
541 ---------+---------+---------+---------+---------+---------+   600
    GACGCGCCGCCACTGGCTGGTTTTCCTCGTCTCTTTCTCAAAAGGCTGCAGAGGTACTAC
    LeuArgGlyGlyAspArgProLysGlyAlaGluLysGluPheSerAspValSerMetMet

GCTCGAAGCTGTTGGGAACCATGGGGCATGTTCCGTAAACCGTTCAGTGGTCCTGCATCC
601 ---------+---------+---------+---------+---------+---------+   660
    CGAGCTTCGACAACCCTTGGTACCCCGTACAAGGCATTTGGCAAGTCACCAGGACGTAGG
    AlaArgSerCysTrpGluProTrpGlyMetPheArgLysProPheSerGlyProAlaSer
```

Figure 2

```
     ACCAACCTACGCACATGGGGAACAGGCGGTCTTCGGCGCATCTCTGATACTGAGCCGTTC
661  ---------+---------+---------+---------+---------+---------+  720
     TGGTTGGATGCGTGTACCCCTTGTCCGCCAGAAGCCGCGTAGAGACTATGACTCGGCAAG
     ThrAsnLeuArgThrTrpGlyThrGlyGlyLeuArgArgIleSerAspThrGluProPhe

AAAGATGTAATTCTCTGCTCACCGACCAGAGGTCGTGAACGTGAAATTGCACCACATCCG
721  ---------+---------+---------+---------+---------+---------+  780
     TTTCTACATTAAGAGACGAGTGGCTGGTCTCCAGCACTTGCACTTTAACGTGGTGTAGGC
     LysAspValIleLeuCysSerProThrArgGlyArgGluArgGluIleAlaProHisPro

TCATTGAAACCACAGCGTTTTTTAAGGCAGGTGGTGCGTGCAGCCTTACCCCTAGGAATT
781  ---------+---------+---------+---------+---------+---------+  840
     AGTAACTTTGGTGTCGCAAAAAATTCCGTCCACCACGCACGTCGGAATGGGGATCCTTAA
     SerLeuLysProGlnArgPheLeuArgGlnValValArgAlaAlaLeuProLeuGlyIle

GGGATTATCTACGACCCCTTTGCTGGTAGCGGTTCCACGCTCGCAGCAGCAGAAGCCGTT
841  ---------+---------+---------+---------+---------+---------+  900
     CCCTAATAGATGCTGGGGAAACGACCATCGCCAAGGTGCGAGCGTCGTCGTCTTCGGCAA
     GlyIleIleTyrAspProPheAlaGlySerGlySerThrLeuAlaAlaAlaGluAlaVal

GGCTATCGTGCTATCGGCACAGATAGAGACGCTCAATACTTTGGGATTGGAACCAAAGCG
901  ---------+---------+---------+---------+---------+---------+  960
     CCGATAGCACGATAGCCGTGTCTATCTCTGCGAGTTATGAAACCCTAACCTTGGTTTCGC
     GlyTyrArgAlaIleGlyThrAspArgAspAlaGlnTyrPheGlyIleGlyThrLysAla

TTTTCATCTCTTTCCACTCTGGATATCAACAAATGA
961  ---------+---------+---------+------  996
     AAAAGTAGAGAAAGGTGAGACCTATAGTTGTTTACT
     PheSerSerLeuSerThrLeuAspIleAsnLysEnd
```

Figure 2 (Cont.)

```
      ATGAATCCAGACGAAGTATTTTCAGACTTTCAGCGTGGTTTTTTTGGAAGAAAATTTACT
  1   ---------+---------+---------+---------+---------+---------+   60
      TACTTAGGTCTGCTTCATAAAAGTCTGAAAGTCGCACCAAAAAAACCTTCTTTTAAATGA
      MetAsnProAspGluValPheSerAspPheGlnArgGlyPhePheGlyArgLysPheThr

GCTGGCCTTCTGGTCTCATTCATTGACTTAATGTCTGAATTAGAAACTCCAAAACTTGGC
 61   ---------+---------+---------+---------+---------+---------+   120
      CGACCGGAAGACCAGAGTAAGTAACTGAATTACAGACTTAATCTTTGAGGTTTTGAACCG
      AlaGlyLeuLeuValSerPheIleAspLeuMetSerGluLeuGluThrProLysLeuGly

ATTGCGGATTTTGATGGCTTTCTAAAGCTATTCCCAAGACAACTAAAAACTAGCGCAGGG
121   ---------+---------+---------+---------+---------+---------+   180
      TAACGCCTAAAACTACCGAAAGATTTCGATAAGGGTTCTGTTGATTTTGATCGCGTCCC
      IleAlaAspPheAspGlyPheLeuLysLeuPheProArgGlnLeuLysThrSerAlaGly

AAACGCGCTAATACTCTAATTGTAGAAAAAGAAGATGGGAAAACTATTTCTCTAAGAAAG
181   ---------+---------+---------+---------+---------+---------+   240
      TTTGCGCGATTATGAGATTAACATCTTTTTCTTCTACCCTTTTGATAAAGAGATTCTTTC
      LysArgAlaAsnThrLeuIleValGluLysGluAspGlyLysThrIleSerLeuArgLys

TTCTATAATTCCATTGAAAAATTTTACCGCGCTGAGCACAAACGCTTCGATTATCCCAGC
241   ---------+---------+---------+---------+---------+---------+   300
      AAGATATTAAGGTAACTTTTTAAAATGGCGCGACTCGTGTTTGCGAAGCTAATAGGGTCG
      PheTyrAsnSerIleGluLysPheTyrArgAlaGluHisLysArgPheAspTyrProSer

GCGGCTCCCCATGCGACCCAAGCGTGGGCTGATTATAAAACTTGGCTTGATGCACTTGTA
301   ---------+---------+---------+---------+---------+---------+   360
      CGCCGAGGGGTACGCTGGGTTCGCACCCGACTAATATTTTGAACCGAACTACGTGAACAT
      AlaAlaProHisAlaThrGlnAlaTrpAlaAspTyrLysThrTrpLeuAspAlaLeuVal

ACTTTCTCCGAAGAACAACTTGGAGAATTACGTGGGCGCGTTAACCAATTTGTCTTAGAC
361   ---------+---------+---------+---------+---------+---------+   420
      TGAAAGAGGCTTCTTGTTGAACCTCTTAATGCACCCGCGCAATTGGTTAAACAGAATCTG
      ThrPheSerGluGluGlnLeuGlyGluLeuArgGlyArgValAsnGlnPheValLeuAsp

ACCCTAAAAAGCCAAGAATTTGATCCAACTTCGGTAAAAGTAGAACCTCCATTATTTCGC
421   ---------+---------+---------+---------+---------+---------+   480
      TGGGATTTTTCGGTTCTTAAACTAGGTTGAAGCCATTTTCATCTTGGAGGTAATAAAGCG
      ThrLeuLysSerGlnGluPheAspProThrSerValLysValGluProProLeuPheArg

ATTCTTCTAGAAAAATTCGAAATGACCGCCCAAAAAGGCGAGCCTACAGGGGCTTCTTTC
481   ---------+---------+---------+---------+---------+---------+   540
      TAAGAAGATCTTTTTAAGCTTTACTGGCGGGTTTTTCCGCTCGGATGTCCCCGAAGAAAG
      IleLeuLeuGluLysPheGluMetThrAlaGlnLysGlyGluProThrGlyAlaSerPhe

CAAGGAATAGTCTTTGGATTTCTTCGAGCCGACAATCCTCATCTTCAAATTGAAATCGAC
541   ---------+---------+---------+---------+---------+---------+   600
      GTTCCTTATCAGAAACCTAAAGAAGCTCGGCTGTTAGGAGTAGAAGTTTAACTTTAGCTG
      GlnGlyIleValPheGlyPheLeuArgAlaAspAsnProHisLeuGlnIleGluIleAsp

AAAGTCCGCACTGGCTCCAAACGACTGCAGCGCATCGGTGATGTCGATGGATGGGAAGGA
601   ---------+---------+---------+---------+---------+---------+   660
      TTTCAGGCGTGACCGAGGTTTGCTGACGTCGCGTAGCCACTACAGCTACCTACCCTTCCT
      LysValArgThrGlySerLysArgLeuGlnArgIleGlyAspValAspGlyTrpGluGly
```

Figure 3

```
       GAACGATTAGCTATCTCCGCTGAAGTAAAACAATATGAAATAAATACTGAATCAATAGAT
  661  ---------+---------+---------+---------+---------+---------+  720
       CTTGCTAATCGATAGAGGCGACTTCATTTTGTTATACTTTATTTATGACTTAGTTATCTA
       GluArgLeuAlaIleSerAlaGluValLysGlnTyrGluIleAsnThrGluSerIleAsp

GACCTTGCTGATTTTGCCAACAGGACTGGTCAGCGTGGCGCGTTGGGGGTTATTGCAGCA
  721  ---------+---------+---------+---------+---------+---------+  780
       CTGGAACGACTAAAACGGTTGTCCTGACCAGTCGCACCGCGCAACCCCCAATAACGTCGT
       AspLeuAlaAspPheAlaAsnArgThrGlyGlnArgGlyAlaLeuGlyValIleAlaAla

TTGAGTTTTAGCGAAGAAGCAAAACCACTTCTAGAAAACATGGGACTAATAGCTCTCGAC
  781  ---------+---------+---------+---------+---------+---------+  840
       AACTCAAAATCGCTTCTTCGTTTTGGTGAAGATCTTTTGTACCCTGATTATCGAGAGCTG
       LeuSerPheSerGluGluAlaLysProLeuLeuGluAsnMetGlyLeuIleAlaLeuAsp

AAAGAAGGTATGCTTAAAATTGTCGAATTATGGGATCCAGTGAAACAAAGAACCGCAGTT
  841  ---------+---------+---------+---------+---------+---------+  900
       TTTCTTCCATACGAATTTTAACAGCTTAATACCCTAGGTCACTTTGTTTCTTGGCGTCAA
       LysGluGlyMetLeuLysIleValGluLeuTrpAspProValLysGlnArgThrAlaVal

AGCTCTTTCATTTACTATGCAACCCATGTCGAGAAAAATTCGAGTTTGAGCGCCCGTCTT
  901  ---------+---------+---------+---------+---------+---------+  960
       TCGAGAAAGTAAATGATACGTTGGGTACAGCTCTTTTTAAGCTCAAACTCGCGGGCAGAA
       SerSerPheIleTyrTyrAlaThrHisValGluLysAsnSerSerLeuSerAlaArgLeu

AACATTTTCCTTGAAGCTTCTGCTTCTGAATGGGCTGAGCAGCGCCAAGCAGCAATTCTC
  961  ---------+---------+---------+---------+---------+---------+  1020
       TTGTAAAAGGAACTTCGAAGACGAAGACTTACCCGACTCGTCGCGGTTCGTCGTTAAGAG
       AsnIlePheLeuGluAlaSerAlaSerGluTrpAlaGluGlnArgGlnAlaAlaIleLeu

CCACAATCAGAATCCTAA
 1021  ---------+--------  1038
       GGTGTTAGTCTTAGGATT
```

Figure 3 (Cont.)

METHOD FOR CLONING AND PRODUCING THE AATII AND ALUI RESTRICTION ENDONUCLEASE AND METHYLASE AND RELATED METHOD FOR OVEREXPRESSING RESTRICTION ENDONUCLEASES

CROSS-REFERENCE TO RELATED APPLICATION

The present application is a continuation-in-part of U.S. application Ser. No. 07/909,947, filed on Jul. 7, 1992, now abandoned, incorporated herein by reference.

BACKGROUND OF THE INVENTION

The present invention relates to recombinant DNA which encodes the AatII restriction endonuclease and modification methylase and the AluI restriction endonuclease and modification methylase, and the production of these enzymes from the recombinant DNA, as well as to related methods for overexpressing endonucleases.

Type II restriction endonucleases are a class of enzymes that occur naturally in bacteria. When they are purified away from other contaminating bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over one hundred and fifty restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the sequences TTTAAA, PuGGNCCPy and CACNNNGTG respectively. *Escherichia coli* RY 13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving an invading foreign DNA molecule each time that the recognition sequence occurs. The cleavage that takes place disables many of the infecting genes and renders the DNA susceptible to further degradation by non-specific endonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. gen. Genet*, 178:717–719 (1980); HhaII: Mann et al., *Gene*, 3:97–112 (1978); PstI: Walder et al., *Proc. Nat. Acad. Sci.*, 78:1503–1507 (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.*, 12:3659–3676 (1984); PaeR7: Gingeras and Brooks, *Proc. Natl. Acad. Sci, USA*, 80:402–406 (1983); Theriault and Roy, *Gene*, 19:355–359 (1982); PvuII: Blumenthal et al., *J. Bacteriol.*, 164:501–509 (1985)).

A third approach, and one that is being used to clone a growing number of systems involves selection for an active methylase gene (see, e.g., U.S. Pat. No. 5,200,333 to Wilson and BsuRI: Kiss et al., *Nucl. Acid. Res.*, 13:6403–6421 (1985)). Since restriction and modification genes are often closely linked, both genes can often be cloned simultaneously. This selection does not always yield a complete restriction system however, but instead often yields only the methylase gene (BspRI: Szomolanyi et al., *Gene*, 10:219–225 (1980); Bcn I: Janulaitis et al., *Gene*, 20:197–204 (1982); Bsu RI: Kiss and Baldauf, *Gene*, 21:111–119 (1983); and Msp I: Walder et al., *J. Biol. Chem.*, 258:1235–1241 (1983)).

In some systems the cloning problem may lie in trying to introduce the endonuclease gene into a host not already protected by modification. If the methylase gene and endonuclease gene are introduced on a common DNA fragment, the methylase gene must modify or protect the host before the endonuclease gene cleaves the host's genome.

Another obstacle to cloning these systems in *E. coli* was discovered in the process of cloning diverse methylases. Many *E. coli* strains (including those normally used in cloning) have systems that resist the introduction of DNA containing cytosine methylation. (Raleigh and Wilson, *Proc. Natl. Acad. Sci. USA*, 83:9070-9074 (1986) ). Therefore, it is also necessary to carefully consider which *E. coli* strain(s) to use for cloning.

When foreign restriction modification systems are cloned and introduced into *E. coli*, sometimes the endonuclease yield is very low compared to the native endonuclease-producing strain probably due to inefficient transcription or translation of the gene in *E. coli*. In some cases, *E. coli* cells carrying a cloned restriction modification system grow poorly probably due to insufficient methylation protection and unregulated constitutive expression of the restriction endonuclease gene. Therefore, a tightly regulated expression system would be desirable in order to express toxic genes such as restriction endonuclease genes in *E. coli*.

It therefore would be desirable to have an expression system which will produce a minimal level of endonuclease under noninduced conditions and produce large amounts of the desired endonuclease upon induction. In this way foreign restriction modification systems can be stably maintained in *E. coli* hosts.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification and would provide the means for production in commercially useful amounts.

SUMMARY OF THE INVENTION

In one embodiment, the present invention relates to a method for overexpressing restriction endonucleases which comprises an expression vector for the expression of the restriction endonuclease gene and a medium or high copy number compatible vector for the expression of a methylase gene. This enables expression of the methylase gene to a level capable of protecting the DNA against the restriction endonuclease of interest in *E. coli*. The preferred expression system consists of an expression vector such as a T7 expression vector for insertion of the endonuclease gene, a second compatible vector which regulates the expression vector, such as a vector containing the T7 lysozyme gene whose gene product inhibits T7 RNA polymerase and reduces the basal level expression of the target gene from the T7lac promoter, and a third compatible plasmid for cloning of the methylase gene. In the preferred embodiment, this third plasmid for methylase gene cloning is a copy-number mutant that has been mutagenized, preferably by UV mutagenesis (J. Miller, *Experiments in Molecular Genetics*, Cold Spring Harbor Laboratory, Cold Spring Harbor, N.Y., pp. 121-124 (1972)), to increase copy number. The expression system of the present invention allows for high level of induction with a low level of constitutive expression and is therefore useful for the expression of toxic proteins in *E. coli* such as restriction endonucleases.

In another embodiment, the present invention relates to recombinant DNA encoding the genes for the AatII restriction endonuclease and modification methylase obtainable from *Acetobacter aceti* as well as related methods for the production of AatII restriction enzyme from the recombinant DNA. This invention also relates to a transformed host which expresses the restriction endonuclease AatII, an enzyme which recognizes the DNA sequence 5'-GACGTC-3' and cleaves between T and C on both DNA strands to leave a 4 base, 3' overhang (H. Sugisaki et al., *Nucl. Acids Res.*, 10:5747-5752). AatII endonuclease produced in accordance with the present invention is substantially pure and free of the contaminants normally found in restriction endonuclease preparations made by conventional techniques as described in Example 1.

One preferred method for cloning the AatII restriction-modification system comprises: selecting an appropriate vector, forming several libraries containing DNA from *Acetobacter aceti*, isolating those clones which contain DNA coding for the AatII modification methylase, cloning additional chromosomal DNA adjacent to the methylase gene using a vector, screening for those clones that produce AatII endonuclease, mapping the aatIIR and aatIIM genes on the clone (aatIIR and aatIIM, genes coding for AatII endonuclease and AatII methylase, respectively), determining the DNA sequences of aatIIR and aatIIM genes, and overexpressing aatIIR and aatIIM genes in *E. coli*.

In a further embodiment, the present invention relates to recombinant DNA encoding the genes for the AluI restriction endonuclease and modification methylase obtainable from *Arthrobacter luteus* as well as related methods for the production of the AluI restriction enzyme from the recombinant DNA. This invention also relates to a transformed host which expresses the restriction endonuclease AluI, an enzyme which recognizes the DNA sequence 5'-AGCT-3' and cleaves between G and C on both DNA strands to leave blunt ends (Roberts et al., *J. Mol. Biol.*, 102:157-165 (1976)). AluI endonuclease produced in accordance with the present invention is substantially pure and free of the contaminants normally found in restriction endonuclease preparations made by conventional techniques as described in Example 4.

One preferred method for cloning the AluI restriction-modification system comprises: selecting an appropriate vector, forming several libraries containing DNA from *Arthrobacter luteus*, isolating those clones which contain DNA coding for the AluI modification methylase, screening for those clones that also produce AluI endonuclease, mapping the aluIR and aluIM genes on the clone (aluIR and aluIM, genes coding for AluI endonuclease and AluI methylase, respectively), determining the DNA sequences of the aluIR and aluIM genes, and overexpressing aluIR and aluIM genes in *E. coli*.

BRIEF DESCRIPTION OF THE FIGURES

FIG. 2 (SEQ IDS: 11 and 12) is the DNA sequence of aatIIM gene and its encoded protein sequence.

FIG. 3 (SEQ IDS: 13 and 14) is the DNA sequence of aatIIR gene and its encoded protein sequence.

DETAILED DESCRIPTION OF THE INVENTION

In a first embodiment, the present invention relates to a method of overexpressing restriction endonucleases, comprising the use of an expression system where the endonuclease gene is contained on an expression vector, and the methylase gene is contained on a separate medium or high copy-number vector compatible with the expression vector.

One preferred embodiment comprises:

1. A T7 expression vector containing the T7lac promoter and ColE1 replication origin, obtainable from Novagen Inc. (J. W. Dubendorff and F. W. Studier, *J. Mol. Biol.*, 219:45-59 (1991)), for cloning of the endonuclease gene, and a second compatible vector containing the p15A replication origin and the T7 lysozyme gene whose gene product inhibits T7 RNA polymerase and reduces the basal level expression of the target gene from the T7 promoter (F. W. Studier, *J. Mol. Biol*, 219:37-44 (1991)). Other expression vectors could be employed, such as pUC19 and pBR322 derivatives containing promoters which can be used for endonuclease expression such as Plac, PlacUV5, Ptac and λPL.

2. A medium-copy number cloning vector containing a pSC101 replication origin for cloning of methylase gene which is expressed from the lac promoter (R. F. Wang and S. R. Kushner, *Gene*, 100:195-199 (1991)). Other increased-copy-number compatible cloning vectors could be generated from low-copy number compatible vectors using for example mutagenesis, preferably UV mutagenesis (J. Miller, supra), such as RP4, RP1, R18, R68, RSF1010, R1162, and R300B (U. Kues and U. Stahl, *Microbiological Reviews*, pp. 491-516 (1989)).

Another embodiment comprises recombinant DNA, including the cloning thereof, which DNA encodes the AatII restriction endonuclease and modification methylase, as well as the method of producing AatII restriction endonuclease from such a recombinant DNA.

Figure 1:
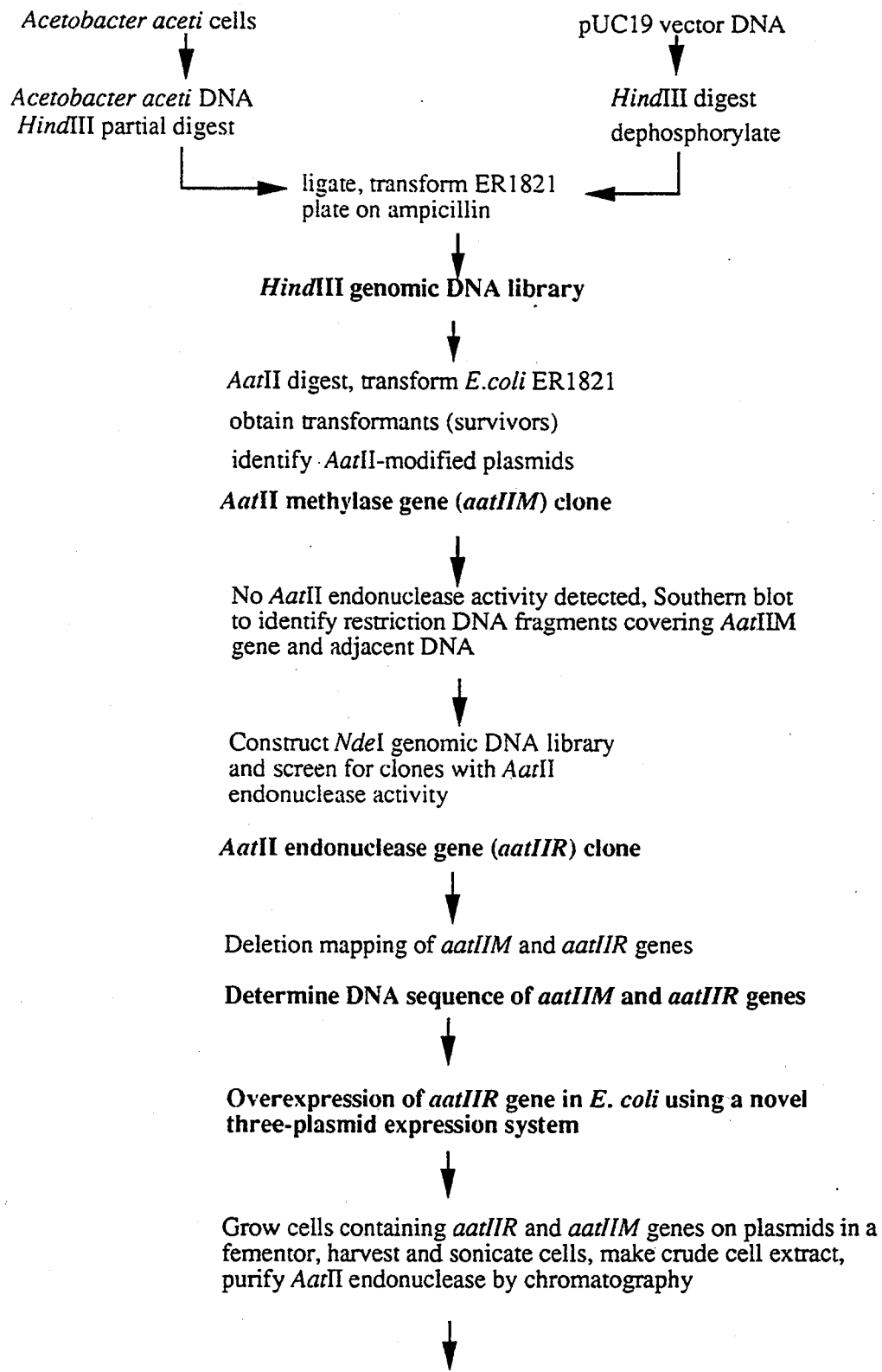
FIG. 1 is a scheme for cloning and producing the AatII restriction endonuclease.

The method described herein by which the AatII restriction gene and methylase gene are preferably cloned and expressed is illustrated in FIG. 1 and includes the following steps:

1. The genomic DNA of *Acetobacter aceti* is purified.

2. The DNA is partially digested with a restriction endonuclease such as HindIII, or any of its isoschizomers, that generates a DNA fragment(s) containing the entire AatII methylase gene. Alternatively, one could make a library which contains the entire restriction modification system such as an NdeI genomic library (skip to step 7). The fragment(s) should also be of cloneable size, that is, between 1.5-14kb.

3. The HindIII-digested genomic DNA is ligated into the pUC19 cloning vector. The resulting mixtures are used to transform an appropriate host, i.e. an hsdR−, mcrBC−, mrr− strain, such as *E. coli* strain RR1. The DNA/cell mixtures are plated on ampicillin selective media for transformed cells. After incubation, the transformed cell colonies are harvested together to form the primary cell libraries. A total of 10 such primary cell libraries were constructed using complete or partial digestion of the *Acetobacter aceti* DNA by the respective cloning endonuclease, and transformed into host strains.

4. The recombinant plasmids are purified in toto from the primary cell libraries to make primary plasmid libraries. The purified plasmid libraries are then digested to completion in vitro with AatII endonuclease which is prepared from *Acetobacter aceti* cells, or any AatII isoschizomer. AatII endonuclease digestion causes the selective destruction of unmodified, non-methylase-containing clones, resulting in an increase in the relative frequency of AatII methylase-carrying clones.

5. Identification of AatII methylase clones: The digested plasmid library DNA is transformed back into a host such as *E. coli* strain RR1 and transformed colonies are again obtained by plating on ampicillin plates. The colonies are picked and their DNA is analyzed for the presence of the AatII methylase gene by incubating purified plasmid DNA in vitro with AatII endonuclease to determine whether it is resistant to AatII digestion.

6. Once it has been established that the methylase gene has been cloned, the clone is assayed for AatII endonuclease activity. If activity is detected, then the AatII restriction gene is linked to the methylase gene and is present in the clone. In such a case one could theoretically then skip to step 7 below. However, in accordance with the present invention, no restriction activity was detected. The lack of restriction activity indicates that either the restriction gene is not linked to the methylase gene, or it is linked but not cloned intact with the methylase gene, or it is cloned intact but not expressed or the entire system has been cloned but expression of the methylase gene is insufficient to fully protect against the restriction endonuclease and the only clones that survive the selection have undergone spontaneous mutations or deletions in the endonuclease gene. In order to determine which of the above possibilities is the situation, the cloned fragment is restriction-mapped and deletions are made to determine the relative position of the methylase gene within the cloned fragment. The information is then used to determine if there is enough DNA on either side of the methylase gene to encode a restriction gene, if they are linked. If there is enough length of DNA, the restriction gene is assumed not to be linked, or to be present in the clone but not expressed (skip to step 10). If there is not enough DNA on both sides of the methylase gene in the cloned DNA to encode a linked restriction gene, as was found for the HindIII clone, p(UC)AatIIM18, of the present invention, a portion of the methylase gene is used to probe digests of the *Acetobacter aceti* chromosome to generate by Southern hybridization a genomic map of the region extending beyond the boundaries of the existing cloned DNA. This data helps identify certain endonucleases such as NdeI that cleave the restriction-modification region into individual fragments that carry the methylase gene as well as larger amounts of adjacent DNA. The exact sizes of the fragments generated by such endonucleases are calculated from the data as well. Presumably, if the restriction and modification genes are found to be linked, such fragments would also encode the restriction gene.

7. Enriched libraries are constructed by digestion of *Acetobacter aceti* DNA with NdeI and ligating the generated fragments into an appropriate vector such as pUC19. Clones carrying DNA containing the methylase gene as well as the adjoining regions can be isolated by methylase selection (U.S. Pat. No. 5,200,333 to Wilson and BsuRI: Kiss et al., *Nucl. Acid. Res.*, 13:6403-6421 (1985)).

8. Identification of restriction gene clones: After methylase selection and transformation, ampicillin resistant transformants are screened for DNA inserts that extend beyond the boundaries of the existing methylase clone. Once such clones are identified, crude cell extracts are prepared from these clones. Cell extracts are diluted by serial dilution, and assayed for AatII endonuclease activity. Clones carrying both aatIIM and aatIIR genes are identified by AatII endonuclease activity assay of their cell extracts and the ability to confer vector backbone resistance to AatII endonuclease cleavage.

9. The region containing aatIIR and aatIIM genes was mapped by deletion mapping and subcloning and DNA sequence determined by dideoxynucleotide termination method (F. Sanger et al., *Proc. Natl. Acad. Sci.*, 74:5463–5467 (1977)).

10. Overexpression: In accordance with another embodiment of the present invention, one preferred approach for overexpression of AatII restriction endonuclease and/or other restriction endonucleases comprises 1) Constructing an increased copy number mutant plasmid containing, for example, the pSC101 replication origin and cloning the aatIIM gene or other methylase gene into the above made medium-copy-number plasmid to premodify and protect an *E. coli* host. The aatIIM gene (or other methylase genes) is expressed from lac promoter. 2) Inserting the restriction endonuclease gene aatIIR downstream of a T7lac promoter on an expression vector, such as pSYX22 (the construction of pSYX22 will be described in detail in example 1). This may be accomplished by incorporating restriction sites in primers to amplify the endonuclease gene by polymerase chain reaction (R. K. Saiki et al., *Science*, 230:1350–1354 (1985)) or introducing restriction sites in the beginning and end of the endonuclease gene by site-directed mutagenesis (T. A. Kunkel, *Proc. Natl. Acad. Sci. USA*, 82:488–492 (1985)). In addition, a strong ribosome binding site (Shine & Dalgarno, *Proc. Natl. Acad. Sci. USA*, 71:1342–1346 (1974)) can be placed in front of the gene to increase translation efficiency. Other promoters which can be used for endonuclease expression are $P_{lac}$, $P_{lacUV5}$, $P_{tac}$, $P_R$, R3 and $\lambda P_L$ on pUC 19 and pBR322 derivatives. However, these promotors are not tightly repressed under noninduced condition and therefore they give a low induction ratio.

The DNA sequence of the aatIIR and aatIIM genes can be synthesized by conventional phosphoramidite or phosphotriester chemistry using codons that are more efficiently utilized in *E. coli*. (Applied Biosystems user bulletins #13, 1988; N. Usman et al., *J. Am. Chem. Soc.*, 109:7845–7854 (1987)).

11. AatII production and purification: The AatII methylase or endonuclease may be produced from clones carrying the AatII methylase gene (or a heterologous methylase) and the overexpressed restriction endonuclease gene by propagation in a fermenter in a rich medium containing antibiotics, for example ampicillin, chloramphenicol, and kanamycin. The cells are thereafter harvested by centrifugation and disrupted by sonication to produce a crude cell extract containing AatII methylase and restriction endonuclease activity. The crude cell extract containing the AatII methylase and endonuclease is purified by standard protein purification techniques such as affinity-chromatography, gel filtration, or ion-exchange chromatography.

As discussed above, the present invention also relates to the recombinant DNA which encodes the AluI restriction endonuclease and modification methylase, as well as to the method of producing the AluI restriction endonuclease from such a recombinant DNA.

The method described herein by which the AluI restriction gene and methylase gene are preferably cloned and expressed includes the following steps:

1. The genomic DNA of *Arthrobacter luteus* is purified.

2. The DNA is partially digested with a restriction endonuclease such as PstI, or any of its isoschizomers, that generates a DNA fragment(s) containing the entire AluI methylase gene or the entire restriction-modification system (skip to step 7). The fragment(s) should also be of cloneable size, that is, between 1.5 and approximately 14kb.

3. The PstI-digested genomic DNA is ligated into a cloning vector such as pBR322. The resulting mixtures are used to transform an appropriate host, i.e., an hsdR−, mcrBC−, mrr− strain, such as *E. coli* strain RR1. The DNA/cell mixtures are plated on ampicillin selective medium for transformed cells. After incubation, the transformed cell colonies are harvested together to form the primary cell libraries. As described below, four such primary cell libraries were constructed using complete or partial digestion of the *Arthrobacter luteus* DNA by the respective cloning endonuclease, and transformed into host strains.

4. The recombinant plasmids are purified in toto from the primary cell libraries to make primary plasmid libraries. The purified plasmid libraries are then digested to completion in vitro with AluI endonuclease which is prepared from *Arthrobacter luteus* cells, or any AluI isoschizomer. AluI endonuclease digestion causes the selective destruction of unmodified, non-methylase-containing clones, resulting in an increase in the relative frequency of AluI methylase-carrying clones.

5. Identification of AluI methylase clones: The digested plasmid library DNA is transformed back into a host such as *E. coli* strain RR1 and transformed colonies are again obtained by plating on ampicillin plates. The colonies are picked and their DNA is analyzed for the presence of the AluI methylase gene by incubating purified plasmid DNA in vitro with AluI endonuclease to determine whether it is resistant to AluI digestion.

6. Once it has been established that the methylase gene has been cloned, the clone is assayed for AluI endonuclease activity. If activity is detected, then the AluI restriction gene is linked to the methylase gene and is present in the clone. In such a case one could then skip to step 9 below. However, in accordance with the present invention, no restriction activity was detected. The lack of restriction activity indicates that either the restriction gene was not linked to the methylase gene, or it was linked but not cloned intact with the methylase gene, or it is cloned intact but not expressed, or the entire system has been cloned but expression of the methylase gene is insufficient to fully protect against the restriction endonuclease and the only clones that survive the selection have undergone spontaneous mutations or deletions in the endonuclease gene. In order to determine which of the above possibilities is the situation, the cloned fragment is restriction-mapped and deletions are made to determine the relative position of the methylase gene within the cloned fragment. The information is then used to determine if there is enough DNA on either side of the methylase gene to encode a restriction gene, if they are linked. If there is enough length of DNA, the restriction gene is assumed not to be linked, or to be present in the clone but not expressed (skip to step 9).

7. Identification of restriction gene clones: After methylase selection and transformation, ampicillin resistant transformants are screened for DNA inserts that extend beyond the boundaries of the existing methylase clone. Once such clones are identified, crude cell extracts are prepared from these clones. Cell extracts are serially diluted and assayed for AluI endonuclease activity. Clones carrying both aluIM and aluIR genes are identified by the presence of AluI endonuclease activity in cell extracts, and the ability of the DNA to resist digestion by AluI endonuclease.

8. The region containing the aluIM gene is mapped by deletion mapping and subcloning and the DNA sequence is determined, (Zhang et al., Nucleic Acids Research, 21:905–911 (1993)). The amino acid sequence of the N-terminus of the purified AluI endonuclease is also determined. The region thought to contain the beginning of the aluIR gene is sequenced and the sequence is translated in all reading frames. These potential protein sequences are compared to the actual N-terminal amino acid sequence to establish the start of the endonuclease gene.

9. Overexpression: As with AatII, one preferred approach for overexpression of AluI restriction endonuclease and/or other restriction endonucleases comprises: 1) Constructing an increased copy number mutant plasmid containing, for example, the pSC101 replication origin and cloning the aluIM gene or other methylase gene into the above made medium-copy-number plasmid to premodify and protect an E. coli host. The aluIM gene (or other methylase gene) is expressed from the tet promoter. 2) Inserting the restriction endonuclease gene downstream of a T7lac promoter on an expression vector, such as pBPA 1. This may be accomplished by incorporating restriction sites in primers to amplify the endonuclease gene by polymerase chain reaction (R. K. Saiki et al., Science, 230:1350–1354 (1985)). In addition, a strong ribosome binding site (Shine & Dalgarno, Proc. Natl. Acad. Sci. USA, 71:1342–1346 (1974)) can be placed in front of the gene to increase translation efficiency, and several copies of a transcription terminator can also be placed upstream of the promoter to prevent read-through transcription by E. coli RNA Polymerases. Other promoters which can be used for endonuclease expression are Plac, PlacUV5, Ptac, PR, T3 and IPL on pBR322 and pUC19 derivatives. However, these promoters are not tightly repressed under noninduced conditions and therefore they give a low induction ratio.

10. AluI production and purification: The AluI methylase or endonuclease may be produced from clones carrying the AluI methylase gene (or a heterologous methylase) and the overexpressed restriction endonuclease gene by propagation in a fermenter in a rich medium containing antibiotics, for example ampicillin (Ap), chloramphenicol (Cm), and kanamycin (Kan). The cells are thereafter harvested by centrifugation, resuspended in a small volume of buffer and disrupted by sonication to produce a crude cell extract containing AluI methylase and restriction endonuclease activity. The crude cell extract containing the AluI methylase and endonuclease is purified by standard protein purification techniques such as affinity-chromatography, gel filtration, or ion-exchange chromatography.

Although the above-outlined steps represent the preferred modes for practicing the present invention, it will be apparent to those skilled in the art that the above described approach can vary in accordance with techniques known in the art.

The following examples are given to illustrate embodiments of the present invention as it is presently preferred to practice. It will be understood that these examples are illustrative, and that the invention is not to be considered as restricted thereto except as indicated in the appended claims.

EXAMPLE 1

1. Cloning of AatII restriction and modification system: The aatIIM gene was first cloned in a HindIII fragment using methylase selection by challenging a plasmid library with AatII endonuclease and looking for survivors after transformation. As discovered later, only part of the aatIIR gene was present in this HindIII insert. Restriction mapping of the Acetobacter aceti genomic DNA indicated that an NdeI fragment should extend one end of the DNA adjacent to the aatIIM gene. The AatII restriction-modification system, aatIIR and aatIIM genes, was cloned in an NdeI restriction fragment in pUC19 vector by the methylase selection method. This clone was named p(UC)AatIIR+M+18 which makes 2000 units of AatII endonuclease per gram of wet E. coli cells. p(UC)AatIIR+M+21 contains the same NdeI insert but in the opposite orietation.

2. Restriction mapping of aatIIM and aatIIR genes: The aatIIM and aatIIR genes were mapped as follows: There are two XbaI sites (about 300 bp apart) in the 5500-bp NdeI fragment insert and one XbaI site in the multiple cloning site of pUC19. An XbaI fragment deletion subclone (a deletion of about 1000 bp) was constructed which deleted out the two XbaI restriction fragments. Two $\mu$g of p(UC)AatIIR+M+18 was digested with 20 units of XbaI in a 1X restriction buffer (50 mM NaCl, 10 mM Tris-HCl, 10 mM MgCl$_2$, 1 mM dithiothreitol) in 50 $\mu$l at 37° C. for 1 hour. The digested DNA was extracted with equal volume of phenol-CHCl$_3$ and CHCl$_3$ and precipitated with ethanol and dried. 0.2 $\mu$g of the resulting DNA was ligated with T4 DNA ligase a 50 $\mu$l in a 1×ligation buffer (50 mM Tris-HCl, 10 mM MgCl$_2$, 10 mM dithiothreitol, 1 mM ATP 25 $\mu$g/ml of bovine serum albumin) at 16° C. overnight. The ligated DNA was diluted by addition of equal volume of sterile-distilled water. 10 $\mu$l of the diluted DNA was mixed with 0.1 ml of ER1821 $\Delta$(hsd-mrr-mcrBC) competent cells and incubated at 4° C. for 30 minutes, 42° C. for 3 minutes. After addition of 0.1 ml of LB medium and incubation at 37° C. for 1 hour the cell/DNA mixture was plated on LB agar plate plus 50 $\mu$g/ml of ampicillin (Ap) and incubated at 37° C. overnight. 12 individual ampicillin resistant (Ap$^r$) transformants were picked and inoculated into 2 ml of LB plus Ap and shaken at 37° C. overnight. 1.5 ml cells each were centrifuged in 1.5 ml Eppendorf tube to make plasmid DNA by a mini-purification procedure adapted from the method of Birnboim and Doly, Nucleic Acids Res., 7:1513–1523 (1979).

Plasmid mini-preparation procedure: 1.5 ml overnight culture was pelleted at 6,000×g for 3 minutes. The supernatant was poured off and the cell pellet was resuspended in 0.2 ml of 25 mM Tris-HCl, pH 8.0, 10 mM EDTA, 50 mM glucose, 20 $\mu$g/ml RNaseA. After five minutes at room temperature, 0.2 ml of 0.2M NaOH, 1% SDS was added and the tube was inverted to lyse the cells. After five minutes at room temperature, 0.15 ml of 3M sodium acetate, pH 4.8, was added and inverted to mix well. The precipitate that formed was spun down at 12,000×g, 4° C. for 10 minutes. The supernantant was removed and extracted with an equal volume of phenol/chloroform (1:1). The layers were separated by centrifugation at 12,000×g for five minutes. The upper phase was taken into a new centrifuge tube and extracted with equal volume of chloroform. The DNA was mixed with 0.9 ml of 95% ethanol. The tube was spun at 12,000×g for 10 minutes to pellet the precipitated nucleic acids. The supernatant was discarded and the pellet was washed again with 1 ml of 70% ethanol, repelleted and dried for 15 minutes under vacuum. Once dry, the pellet was resuspended in 100 μl of TE buffer (10 mM Tris-HCl, 1 mM EDTA, pH 8.0).

Twelve plasmid DNA were analyzed by XbaI endonuclease digestion and agarose gel electrophoresis to confirm the XbaI deletion. All of them contain the correct size deletion. The XbaI deletion clone, p(UC)AatIIM+(XbaIΔ), still contains the intact aatIIM gene because when challenged with AatII endonuclease the plasmid DNA is resistant to AatII cleavage. To further narrow down the size of aatIIM gene an EcoO1091 fragment was deleted between the EcoO1091 site on the vector and an EcO01091 site on the remaining insert. This deletion was constructed in the same way as the XbaI deletion except the EcoO1091 ends were first filled-in with Klenow fragment of E. coli DNA polymerase I and then self-ligated. The resulting EcoO 1091 deletion clone was partially resistant to AatII endonuclease digestion, indicating that the aatIIM gene is still contained in the clone. The XbaI deletion clone and the EcoO1091 deletion clone defined the aatIIM within a DNA fragment of approximately 1800 bp. The XbaI deletion clone was also assayed for AatII endonuclease activity to see if it contains the intact aatIIR gene. Crude cell extract was prepared as follows: 200 ml LB plus Ap were inoculated with 2 ml of overnight cells and shaken at 37° C. overnight. The cells were centrifuged and cell pellet resuspended in 20 ml sonication buffer (10 mM Tris-HCl, 10 mM β-mercaptoethanol), sonicated for ten times at 30 seconds burst, centrifuged at 15000×g for 30 minutes to remove cell debris. 1 μl, 2 μl, 4 μl, and 8 μl of cell extract was incubated with 1 μg of λDNA at 37° C. for one hour in 30 μl in a 1×AatII restriction buffer (50 mM potassium acetate, 20 mM Tris actate, 10 mM magnesium acetate, 1 mM dithiothreitol). Three μl of stop sulution was added and DNA was analyzed by agarose gel electrophoresis. No AatII endonuclease activity was found in the XbaI deletion clone, indicating part of the endonuclease gene has been deleted.

In order to map the boundaries of aatIIR gene, the aatIIM gene was first cloned into a vector pR976, a pACYC184 derivative containing $P_{tac}$ and multiple cloning sites (constructed by Paul Riggs, New England Biolabs, Beverly, Mass.). A 3000 bp PstI fragment containing the aatIIM gene was inserted into the PstI site of pR976. The resulting plasmid, pR976AatIIM+, was transformed into E. coli strain ER1821 Δ(hsd-mrr-mcrBC). Deletion subclones were transformed into premodified ER1821 [p(R976)AatIIM+]to see whether they contain intact aatIIR gene.

There are two HincII sites in p(UC)AatIIR+M+18, one in the multiple cloning sites of the vector and the other in the insert. A HincII deletion, a deletion of about 4500 bp, was constructed in the same way as the XbaI deletion clone. When this plasmid was transformed into ER1821 [p(R976)AatIIM+] cells, and cell extracts were prepared from the transformants, no AatII endonuclease activity was detected. Another deletion clone contains an EcoRV/SmaI fragment deletion which deleted about 4200 bp DNA. This deletion clone shows AatII endonuclease activity in crude cell extract. These results showed that the aatIIR gene is within a DNA fragment of appoximately 1300 bp.

3. DNA sequence analysis of aatIIM and aatIIR genes: In order to sequence the DNA region containing both aatIIM and aatIIR genes, four more deletion subclones (BamHI fragment deletion, EcoRI fragment deletion, HindIII fragment deletion, and PstI fragment deletion) were constructed in the same way as was done for the XbaI fragment deletion by the respective endonuclease cleavage and self-ligation. A total of 3365 bp DNA was sequenced on both strands by Sanger dideoxy-termination sequencing method (F. Sanger et. al., Proc. Natl. Acad. Sci. USA, 74:5463–5467). Two large open reading frames, 996 bp and 1038 bp, respectively, were found in the region in which the aatIIM and aatIIR genes were mapped. Subcloning of the 996 bp open reading frame in a plasmid showed AatII site modification and thus this open reading frame was assigned to aatIIM gene (FIG. 2, SEQ IDS: 11 and 12). The predicted amino acid sequence from the aatIIM gene showed that it contains conserved motifs for the N-6 adenine methylases (motifs DPPY and DPF-GSG-T). Subcloning of the 1038 bp open reading frame in a plasmid and transforming into AatII methylase-modified cells showed AatII endonuclease activity in crude cell extract. Thus this open reading frame was assigned to aatIIR gene (FIG. 3, SEQ IDS: 13 and 14).

4. Overexpression of aatIIR gene in E. coli:

A. Expression of aatIIM and aatIIR gene under $\lambda P_L$ promoter: A BspEI/NdeI DNA fragment containing both aatIIM and aatIIR genes was cloned into expression vector pDNEV5, a derivative of pUC19 that contains the $\lambda P_L$ promoter and λ temperature-sensitive repressor gene $cI_{857}$ (pDNEV5 constructed by Donald Nwankwo, New England Biolabs, Beverly, Mass.). The resulting plasmid was named p(DNEV5)AatIIR+M+. ER1821 [p(DNEVS)AatIIR+M+] cells make 40,000 units of AatII endonuclease per gram of wet cells after induction at 43° C. overnight. The yield is 20 times higher than the native Acetobacter aceti strain. This overproducing strain, however, is not stable. It grew poorly in a 100 liter fermentor and some cells were lysed in the culture. Therefore, construction of more stable clones were attempted.

B. Expression of aatIIR gene under $P_{tac}$ promoter: In order to stabilize the AatII endonuclease producing clone, the aatIIM gene contained within a PstI/NdeI fragment was subcloned into pUC19. The four AatII sites in the resulting plasmid, p(UC)AatIIM+(PstI/NdeI) were completely modified by the AatII methylase. An EcoRI restriction fragment carrying the aatIIR gene was cloned into a compatible expression plasmid pR976 under $P_{tac}$ promoter and Lac repressor control. When E. coli cells ER2267 [p(UC)AatIIM+(PstI/NdeI), p(R976)-AatIIR+(EcoRI/EcoRI)] were induced by addition of 0.5 mM IPTG in a 1 liter cell culture, AatII endonuclease yield was 10,000 units per gram of wet cells, a 5-fold overexpression over the native Acetobacter aceti strain. However, when the culture was scaled up to 100 liter fermenter, the yield dropped to 2000 units per grams of wet cells. The reason for the failure to scale up is unknown.

C. Expression of aatIIR gene under $P_{lacUV5}$ promoter on expression vector pRRS: 1) Cloning of aatIIM gene into pWSK 129. Plasmid pWSK 129 is a low-copy-number plasmid that contains kanamycin resistance (Kan$^r$) gene and pSC101 replication origin which is compatible with ColE1 origin carried on pUC19 and pBR322 derived vectors (R. F. Wang and S. R. Kushner, *Gene*, 100:195–199 (1991)). Plasmid pWSK 129 also contains multiple cloning sites flanked by T7 and T3 RNA polymerase promotors. The aatIIM gene was amplified by PCR from p(UC)AatIIR+M+21 using two primers (Primer 1 has a BamHI site near the 5' end: 5' CGG GAT CCG GAG GAA TAA AAT GAC CGC TCG TCC 3', SEQ ID: 1; Primer 2 contains a PstI site near the 5' end: 5' CCT TAA CTG CAG TCA TTT GTT GAT ATC CAG AG 3', SEQ ID:2). The PCR products were purified and cleaved with BamHI and PstI and ligated into BamHI/PstI digested pWSK 129. The ligated DNA was used to transform *E. coli* ER2206 cells and transformants were selected for kanamycin resistance. Eighteen individual transformants were screened for aatIIM insert in mini-preparation plasmid DNA. Eleven transformants contained the correct size insert and the resulting plasmid was named p(WSK129)Aat-IIM+. The plasmid is resistant to AatII digestion, indicating full modification by AatII methylase. 2) Cloning of aatIIR gene into expression vector pRRS2: Expression vector pRRS is a pUC19-derived vector that contains a lacUV5 promoter, a multiple cloning sequence, and a positive retroregulator stem-loop element downstream of the multiple cloning site (C. M. Skoglund et al., *Gene*, 88:1–5 (1990)). A pRRS derivative, pRRS2, was constructed by filling-in the EcoRI site distal to the lacUV5 promoter and inserting a new EcoRI linker into the HindIII site proximal to the promoter. Two primers were used to amplify the aatIIR gene from p(UC)Aat-IIR+M+21. Primer 1 contains an EcoRI site and ribosome binding site (5' CTG AAT TCG GAG GTT TAA AAT ATG AAC CCA GAC GAA GTA TTT TCA 3', SEQ ID:3). A SalI site was engineered in primer 2 (5' TCG AGG GTC GAC TTT AGG ATT CTG ATT GTG GGA 3', SEQ ID:4). The aatIIR gene was amplified by PCR reaction with Vent® DNA polymerase (95° C. for 1 minute, 50° C. for 2 mintues, 72° C. for 1 minute, 20 cycles). The DNA products were extracted twice with phenol-CHCl$_3$ and twice with CHCl$_3$ and ethanol-precipitated. After restriction digestion with EcoRI and SalI for 1 hour at 37° C., the DNA was extracted again with phenol-CHCl$_3$ and CHCl$_3$, ethanol-precipitated, dried, and resuspended in 100 μl of TE buffer. The aatIIR gene was ligated into EcoRI/SalI cleaved pRRS2 and transformed into ER2206 [p(WSK 129)AatIIM+]/F' lacI$^q$, Tn 10 (Tc$^r$). Two kinds of colony morphology were observed among the transformants, one of which is normal colonies, and the other is flat, translucent colonies. The latter contain aatIIR insert in pRRS2 and produced AatII endonuclease in 10 ml small culture. It failed to make AatII endonuclease in 200 ml subculture, indicating the clone is not stable. The instability is probably caused by under methylation because the copy number of pUC19-derived vector can be as high as 400 per cell, but the copy number of the methylase containing plasmid is only about 6–8 copies per cell. The other reason may be that there is not sufficient Lac repressor produced in the cell to repress aatIIR gene expression under non-induced condition since the lacI$^q$ gene is carried on the F' low-copy-number plasmid. A tightly regulated expression system is needed for AatII expression.

D. Construction of a medium-copy-number vector for expression of aatIIM gene in *E. coli*: In order to stably overexpress AatII endonuclease, an increased copy-number mutant plasmid was isolated from pWSK 129 as follows: XL 1-Blue cells carrying pWSK 129 was grown to 2×10$^8$ cells/ml in LB plus 50 μg/ml of kanamycin (Kan) and concentrated 10-fold by spining down the cells and resuspending in one tenth volume of 10 mM Tris-HCl, 10 mM MgSO$_4$, pH 7.8. The cells were mutagenized with 15 seconds UV treatment (6 J per second). The mutageneized cells were plated on 2 mg/ml Kan plate which is 40 times more Kan than the regular Kan plate and incubated at 37 ° C. overnight. Thirty-five Kan$^r$ colonies were found and pooled together and innoculated into 10 ml of LB plus 2 mg/ml Kan. To eliminate those clones that are capable of growing in 2 mg/Kan due to host mutations, plasmid DNA was prepared from 1.5 ml overnight culture and retransformed into a new host ER1821 and plated on 2 mg Kan/ml plate. To estimate the plasmid copy number, Kan$^r$ transformants were grown in LB plus kan and plasmid DNA prepared from equal number of cells by a mini-preparation method in parallel with pWSK 129 and pBR322 plasmids. Five ml of the pWSK 129, the copy number mutant, and pBR322 DNA were analyzed by agarose gel electrophoresis. A picture was taken from the ethidium bromide stained DNA in the gel. The negative of the picture was scanned by densitometry to estimate the relative amount of DNA in each lane. It was found that one mutant (#3) increased plasmid copy number 3-fold (18–24 copies per cell). This plasmid was named pSYX 19. To clone the aatIIM gene into pSYX19 two primers were designed to amplify aatIIM gene in such a way that the first primer annealed to the beginning of aatIIM gene on the top strand (Watson strand) and the second primer annealed to the end of the aatIIM gene on the bottom strand (Crick strand). Primer 1 (5' CGG GAT CCG GAG GAA TAA AAT GAC CGC TCG TCC 3', SEQ ID: 1) contains a BamHI site and an efficient ribosome binding site 6 bases upstream of the ATG start codon. Primer 2 (5' CCT TAA CTG CAG TCA TTT GTT GAT ATC CAG AG 3', SEQ ID:2) contains a PstI site near the 5' end. The aatIIM gene was amplified with Vent®DNA polymerase (New England Biolabs, Inc.) by polymerase chain reaction (95° C. for 1 minute, 50° C. for 2 mintues, 72° C. for 1 minute, 20 cycles). The DNA products were extracted twice with phenol-CHCl$_3$ and twice with CHCl$_3$ and ethanol-precipitated. After restriction digestion with BarnHI and PstI for 1 hour at 37° C., the DNA was extracted again with phenol-CHCl$_3$ and CHCl$_3$, ethanol-precipitated, dried,-and resuspended in 100 μl of TE buffer. Five μg of pSYX 19 vector DNA was also cleaved with BamHI and PstI, extracted with phenol-CHCl$_3$ and CHCl$_3$, and ethanol-precipitated, and resuspended in 100 μl of TE buffer. Ten μl of aatIIM DNA and ten μl of the pSYX19 vector DNA was ligated overnight at 16° C. in a 1X ligation buffer in 30 μl total volume. The ligated DNA was diluted by addition of 70 μl of sterile-distilled water and 10 μl DNA was used to transform ER1821 cells and plated on Kan (50 μg/ml) plate. Eighteen Kan$^r$ transformants were grown overnight in 1.5 ml LB plus kanamycin and plasmid DNA was prepared from these overnight cultures. Eleven out of eighteen contain the correct size insert by BamHI and PstI restriction digests. When five of them were digested with AatII endonuclease, all five plasmids are resistant to AatII digestion. One plasmid was named p(SYX19)AatIIM+ and used for co-expression of AatII endonuclease.

Expression of aatllR gene in a medium-copy-number plasmid under T7lac promoter: pET-11a is a T7 expression vector derived from pBR322 that contains a lac operator 4 bp down stream of the T7 promoter (This T7 promoter plus lac operator is called T7lac promoter), the lacI$^q$ gene, and two restriction sites, NdeI and BamHI, for cloning (J. W. Dubendorff and F. W. Studier, *J. Mol. Biol*, 219:45–59 1991)). A pET-11a derivative, pAII17, was constructed that contains four copies of rrnB transcription terminator (pAII17 constructed by William Jack at New England Biolabs, Beverly, Mass.) Upstream of the T7 promoter. The transcription terminator upstream of T7 promoter further decreases basal level of expression of the target gene. Since a BamHI site occurs in the aatllR gene, the BamHI site on the vector was filled-in with klenow fragment of *E. coli* DNA polymerase I and a SalI linker was inserted to replace the BamHI site. This plasmid was named pSYX22. Two primers were designed in such a way that the first primer contains an NdeI site which annealed to the start of aatllR gene and a SalI site was engineered into the second primer which is complementary to the end of the aatllR gene (primer 1: 5' CAA CAT ATG AAT CCA GAC GAA GTA TTT TCA 3', SEQ ID:5; primer 2: 5' TCG AGG GTC GAC TTT AGG ATT CTG ATT GTG GGA 3', SEQ ID:6). The aatllR gene was amplified by PCR with Vent® DNA polymerase (95° C. for 1 minute, 50° C. for 2 mintues, 72° C. for 1 minute, 20 cycles). PCR products were purified by phenol-CHCl$_3$ and CHCl$_3$ extractions and ethanol-precipitation, and cleaved with NdeI and SalI. The DNA was again purified by phenol-CHCl$_3$ and CHCl$_3$ extraction and ethanol-precipitation and resuspended in 100 μl of TE buffer. 10 μl of the aatllR DNA was ligated into 0.5 μg of NdeI/SalI treated pSYX22 at 16° C. overnight. The ligated DNA was diluted with the addition of 70 μl of sterile-distilled water and 10 μl of which was used to transform BL21 (λDE3) Δ(hsd-mrr-mcrBC)[p(SYX19)AatIIM+, Kan$^r$; pLysS, Cm$^r$] and plated on LB agar plus Ap (50 μg/ml), Cm (30 μg/ml), Kan (50 μg/ml). Plasmid pLysS encodes phage T7 lysozyme which inhibits T7 RNA polymerase to reduce the basal level target gene expression from the T7lac promoter (F. W. Studier, *J. Mol. Biol.*, 219:37–44 (1991)). Plasmid DNA was prepared from 1.5 ml culture of 12 individual transformants and analyzed for aatllR DNA insert. Four plasmids contain the correct size insert. One clone, p(SYX22)AatIIR+ was tested for AatII endonuclease activity as follows: 200 ml rich broth medium plus Ap (50 μg/ml), Cm (30 μg/ml), Kan (50 μg/ml) were inoculated with 2 ml overnight cells and shaken at 37° C. to cell density of Klett 100 (midlog phase). IPTG inducer was added to the culture to 0.5 mM final concentration. The cells were induced for two hours and harvested at Klett 175. Cells were pelleted by centrifugation at 4° C., 5000×g for 15 minutes, resuspended in 20 ml sonication buffer (10 mM Tris-HCl, pH 7.8, 10 mM β-mercaptoethanol), and sonicated on ice for ten times at 30 seconds burst. Cell debris was removed by centrifugation at 4° C. 15000×g for 30 minutes. The supernatant was transferred to a new tube and diluted $10^1$-, $10^2$-, $10^3$-, and $10^4$-fold in sonication buffer and 2 μl of the diluted extract was used to cleave 1 μg of HindIII-linearized pUC19 in 1×AatII restriction buffer in a total volume of 30 μl. There is a single AatII site in pUC19. When the HindIII-linearized pUC19 was cleaved with AatII endonuclease, two fragments, 51 6 bp and 2170 bp in size, were generated. After one hour at 37° C. the reaction was stopped by addition of 3 μl of stop solution and DNA analyzed by agarose gel electrophoresis. It was found that a complete digestion was achieved with as little as a 100 fold diluted cell extract. It was estimated that this clone makes $10^6$ units of AatII endonuclease per gram of wet cells. One unit of AatII is that amount of enzyme that will completely digest one μg of λDNA in one hour at 37° C. in a 50μl reaction.

Stability test: BL21 (λDE3) Δ(hsd-mrr-mcrBC) [p(SYX22)AatIIR+, p(SYX19)AatIIM+, pLysS] cells were frozen in 25% glycerol at −70° C. overnight. Cells were streaked out on LB agar plus Ap, Cm, and Kan from the frozen stock to obtain a single colony. 500 ml of rich broth plus antibiotics was inoculated with a single colony and shaken overnight. Colony-forming units were determined from the overnight culture on rich agar plate or rich agar plate supplemented with Ap, Cm, and Kan. It was found that the overproducing strain has the same plating efficiency on both plates ($1.5×10^9$ colony forming units/ml). Five ml of the overnight culture was inoculated into 500 ml of fresh rich broth plus antibiotics and grown to Klett units 100. The culture was induced by addition IPTG to 0.5 mM and incubation continued at 37° C. Cells were recovered by centrifugation. Cell extract was prepared and AatII endonuclease activity determined on linear pUC19 DNA. At least $10^6$ units AatII endonuclease/gram of wet cells were detected.

6. Purification of AatII restriction endonuclease from AatII overproducer strain (NEB #725) a deposit of which has been deposited at the American Type Culture Collection on Jul. 7, 1992 and has received accession no. 69028: Two liters of rich broth medium plus 50 μg/ml Ap, 30 μg Cm/ml, 50 μg/ml Kan were inoculated with 20 ml of overnight BL21 cells carrying the AatII overproducing plasmid p(SYX22)AatIIR+, p(SYX19)AatIIM+, and pLysS. Cells were grown to mid-log phase (Klett units 100) at 37° C. IPTG inducer was added to the culture to a final concentration of 0.5 mM and incubation continued for 2 hours. Cells were centrifuged at 5000×g at 4° C. for 20 minutes and cell pellet resuspended in 80 ml of sonication buffer (10 mM Tris-HCl, pH 7.8, 10 mM β-mercaptoethanol) and sonicated. The following purification procedure was done at 4° C. The extract was centrifuged at 15000×g for 30 minutes and supernatant applied onto a DEAE sepharose column (1.5×15 cm). A salt gradient was applied from zero to 1M NaCl and fractions collected and assayed for AatII endonuclease activity. The fractions containing AatII endonuclease were pooled and dialyzed against a buffer containing 75 mM NaCl, 10 mM KPO4, pH 7, 1 mM DTT, 1 mM EDTA. The enzyme mixture was applied onto a heparin sepharose column (1.5×15 cm) and proteins eluted with a gradient of zero to 1M NaCl. The fractions containing AatII endonuclease were pooled as before and dialyzed against a 0.15M NaCl buffer. The solution was applied to a 1.5×15 cm phophocellulose column and a gradient from 0.15M to 1M NaCl applied. The fractions with AatII endonuclease were pooled and dialyzed against a storage buffer (50% glycerol, 50 mM KCl, 10 mM Tris-HCl, pH 7.4, 0.1 mM EDTA, 1 mM DTT, and 200 μg/ml BSA). The final yield is $10^6$ units of AatII endonuclease from 9 grams of cells (240,000 units AatII/ml). The enzyme was diluted 10-fold to 24,000 units/ml and 2 μl to 10 μl of the diluted enzyme was analyzed by SDS-polyacrylamide gel electrophoresis. IPTG-induced and uninduced cell extracts were also loaded onto the same gel.

Figure 4:
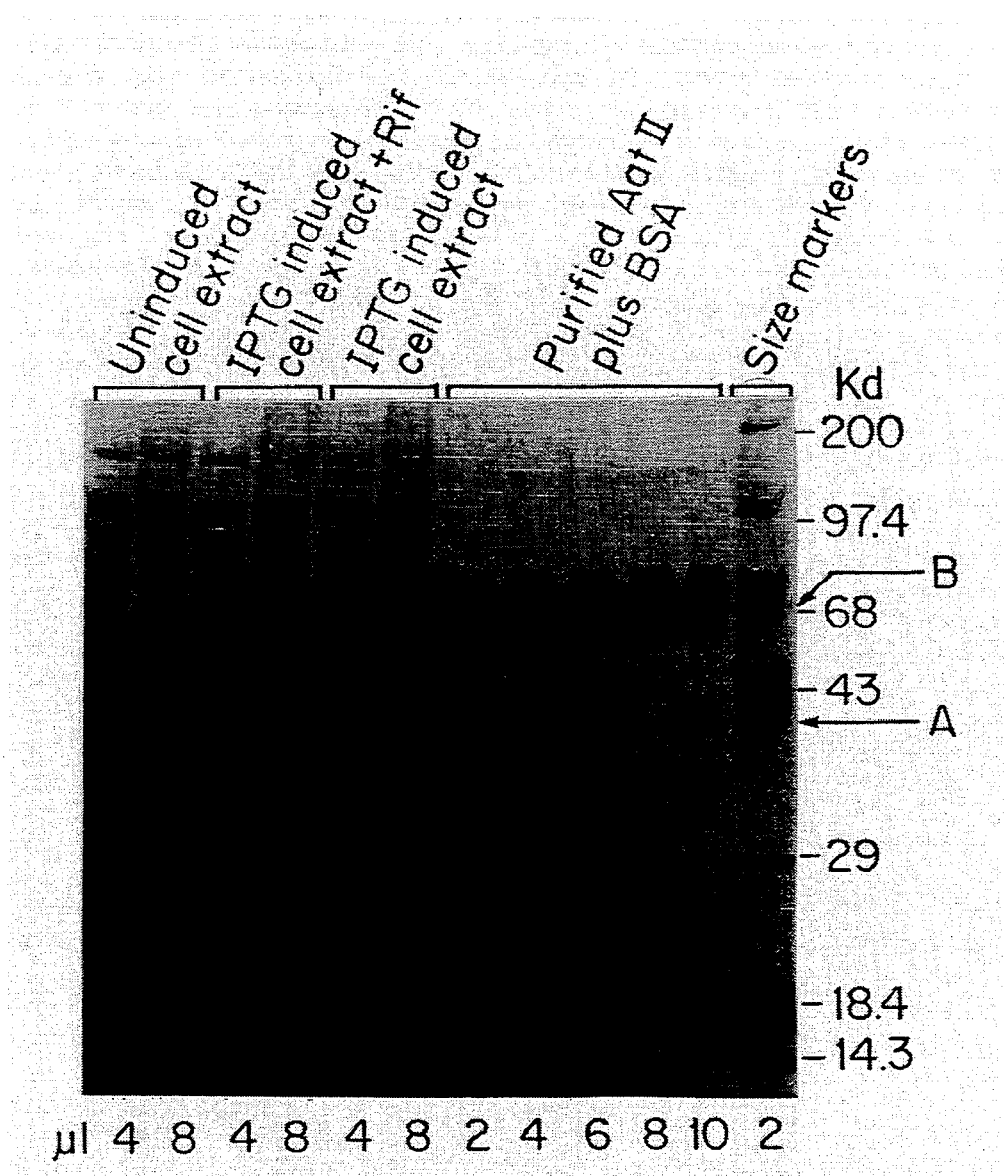
FIG. 4 shows IPTG-induced and uninduced cell extracts and purified AatII endonuclease protein. Arrow A and B indicate AatII endonuclease protein and bovine serum albumin (BSA), respectively.

The result shown in FIG. 4 indicated that the purified AatII endonuclease protein is at least 90% pure. (Note: the 68,000 dalton bovine serum albumin was not a contaminating protein. It was added into the AatII enzyme preparation to stablize the AatII endonuclease).

The AatII restriction endonuclease obtained from this purification was substantially pure and free of non-specific endonuclease and exonuclease. The purity of the AatII restriction endonuclease preparation was checked by looking at the following criteria: 1) Ligation: After a 10-fold overdigestion of λDNA, greater than 90% of the DNA fragments produced were ligated with T4 DNA Ligase. 95% of the ligated fragements could be recut with AatII. 2) Prolonged digestion: After incubating a 50 μl reaction containing 1 μg of λDNA and 72 units of enzyme for 16 hours, the same pattern of DNA bands was produced as a reaction performed in one hour with one unit of enzyme. 3) Exonuclease Activity: After incubation of 72 units of enzyme for 4 hours at 37° C. in a 50 μl reaction containing 1 μg sonicated $^3$H DNA ($10^5$ cpm/μg)less than 0.01% radioactivity was released. All tests were performed in the following reaction buffer: 50 mM potassium acetate, 20 mM Tris actate, 10 mM magnesium acetate, 1 mM dithiothreitol.

EXAMPLE 2

Overexpression of NlaIII endonuclease in *E. coli:* The NlaIII methylase gene (nlaIIIM) and NlaIII endonuclease gene (nlaIIIR) were cloned (see EPO publication no. 477,532, published Apr. 1, 1992) and sequenced. Patent application relating to the methods for NlaIII cloning and production of NlaIII endonuclease from the clone has been filed (U.S. patent application No. 07/575,285). Here we describe a method for overexpression of NlaIII endonuclease in *E. coli* using the expression system of the present invention.

In order to construct a constitutive expression vector, a BssHII restriction fragment containing the lacZa gene was deleted from pSYX19 and an SspI/PvuII restriction fragment carrying the tetracycline resistance (Tc$^r$) gene was ligated with the remaining DNA. The resulting plasmid pSYX20 contains both Kan$^r$ gene and Tc$^r$ gene, a deposit of which has been deposited at the American Type Culture Collection on Jul. 7, 1992 and has received accession no. 75260. Cloning DNA into the Tc$^r$ gene inactivates it, which provides an easy screening method for detection of insert. The unique EcoRV, BamHI, SalI and SphI restriction sites are convenient sites for cloning into the Tc$^r$ gene. A foreign gene inserted can be expressed constitutively from the Tc promoter.

1. Cloning of nlaIIIM gene into pSYX20 vector: Plasmid pSYX20 is a medium-copy-number plasmid that carries Kan$^r$ and Tc$^r$ genes and a pSC101 replication origin. The nlaIIIM gene inserted into the Tc$^r$ gene can be expressed constitutively from the Tc promoter. Two primers were used to amplify the nlaIIIM gene from p(UC)NlaIIIR+M+. Primer 1 contains a BamHI site near 5' end and an efficient ribosome binding site 7 bp upstream of ATG start codon (5' CGG GAT CCG GAG GTT AAT TAA ATG AAC TAC ATC GGC TCC AAA CTA 3', SEQ ID:7). Primer 2 has a SalI site near the 5' end (5' CAA GTC GAC TTA AAA GGT CTT TTC TAA AAT ATG 3', SEQ ID:8). The nlaIIIM gene was amplified with Vent® DNA polymerase by polymerase chain reaction (95° C. for 1 minute, 50° C. for 2 mintues, 72° C. for 1 minute, 20 cycles).

The PCR products were extracted twice with phenol-CHCl$_3$, twice with CHCl$_3$, ethanol-precipitated, and resuspended in 100 μl of TE buffer. After restriction digestion with BamHI and SalI for 1 hour at 37° C., the DNA was extracted again with phenol-CHCl$_3$ and CHCl$_3$, ethanol-precipitated, dried, and resuspended in 100 μl of TE buffer. Five μg of pSYX20 vector DNA was also cleaved with BamHI and SalI, extracted with phenol-CHCl$_3$ and CHCl$_3$, and ethanol-precipitated, and resuspended in 100 μl of TE buffer. Ten μl of nlaIIIM DNA and ten μl of the pSYX20 vector DNA was ligated overnight at 16° C. in a 1X ligation buffer in 30 μl total volume. The ligated DNA was diluted by addition of 70 μl of sterile-distilled water and 10 μl DNA was used to transform ER1821 cells and plated on Kan (50 μg/ml) plate. Eighteen Kan$^r$ transformants were grown overnight in 1.5 ml LB plus Kan and plasmid DNA were prepared and analyzed by BamHI and SalI restriction digestion. Four clones contain the correct size insert. When they were challenged with NlaIII endonuclease, all four plasmids were resistant to NlaIII digestion, indicating full modification by NlaIII methylase. One plasmid was named p(SYX20)NlaIIIM+ and used to transform BL21 (λDE3) Δ(hsd-mrr-mcrBC) [pLysS] cells and plated on LB agar plate plus 30 μg/ml of Cm, 50 μg/ml of Kan. Cm$^r$ and Kan$^r$ transformants were obtained and used later as the host for expression of NlaIII endonuclease.

2. Cloning of nlaIIIR gene into expression vector pSYX22. Expression vector pSYX22 contains the T7lac promoter, the lacI$^q$ gene, two restriction sites, NdeI and SalI, for translation fusion cloning. The construction of pSYX22 has been described in Example 1. Two primers were designed in such a way that the first primer contains an NdeI site which annealed to the start of nlaIIIR gene and a SalI site was engineered into the second primer which is complementary to the end of the nlaIIIR gene (primer 1: 5' TTG CAT ATG AAA ATC ACA AAA ACA GAA CTA 3', SEQ ID:9; primer 2: 5' CGA GTC GAC TCA TCC GTT ATC TTC TTC ATA TAA 3', SEQ ID: 10). The nlaIIIR gene was amplified from p(UC)NlaIIIR+$^1M$+ by PCR with Vent® DNA polymerase (95° C. for 1 minute, 50° C. for 2 mintues, 72° C. for 1 minute, 20 cycles). PCR products were purified by phenol-CHCl$_3$ and CHCl$_3$ extractions and ethanol-precipitation, and cleaved with NdeI and SalI. The DNA was again purified by phenol-CHCl$_3$ and CHCl$_3$ extraction and ethanol-precipitation and resuspended in 100 μl of TE buffer. 10 μl of the nlaIIIR DNA was ligated into 0.5 μg of NdeI/SalI treated pSYX22 at 16° C. overnight. The ligated DNA was diluted with the addition of 70 l of sterile-distilled water and 10 μl of which was used to transform *E. coli* strain ER2267 recA1 Δ(hsd-mrr-mcrBC) and plated on Ap plates. Fourty eight individual transformants were inoculated into 2 ml of LB plus Ap and shaken overnight at 37° C. Plasmid DNA was prepared and analyzed by NdeI and SalI restriction digestion. Ten plasmids contain the correct size insert. One clone p(SYX22)-NlaIIIR+ (#4) was used to transform BL21 (λDE3) Δ(hsd-mrr-mcrBC) [p(SYX20)NlaIIIM+, pLysS] and selection for transformants was on LB agar plus Ap (50 μg/ml), Cm (30 μg/ml), Kan (50/μg/ml). Plasmid pLysS encodes phage T7 lysozyme which inhibits T7 RNA polymerase to reduce the basal level target gene expression from the T7lac promoter (F. W. Studier, *J. Mol. Biol.,* 219:37–44 (1991)). *E. coli* strain BL21 (λDE3) Δ(hsd-mrr-mcrBC) [p(SYX22)NlaIIIR+, p(SYX20)NlaIIIM+, pLysS] was tested for NlaIII endonuclease production as follows: 200 ml of rich broth medium plus Ap (50 μg/ml), Cm (30 μg/ml), Kan (50 μg/ml) were inoculated with 2 ml of overnight cells and shaken at 37° C. to cell density of Klett 75. IPTG inducer was added to the culture to 0.5 mM final concentration. The cells were induced for two hours and harvested at Klett 175. Cells were pelleted by centrifugation at 4° C., 5000×g for 15 minutes, resuspended in 20 ml of sonication buffer (10 mM Tris-HCl, pH 7.8, 10 mM β-mercaptoethanol), and sonicated on ice ten times with 30 second bursts. Cell debris was removed by centrifugation at 4° C. 15000×g for 30 minutes. The supernatant was transferred to a new tube and diluted $10^{-1}, 10^{-2}, 10^{-3}$, and $10^{-4}$-fold in the sonication buffer and 5 μl of the diluted extract was used to cleave 1 μg of λDNA in 1×NlaIII restriction buffer in a total volume of 30 μl. After one hour digestion at 37° C. the reaction was stopped by addition of 3 μl of stop solution and DNA analyzed by agarose gel electrophoresis. It was found that a complete digestion was achieved at $10^{-3}$ dilution of cell extract. It was estimated that this clone makes $2 \times 10^6$ units of NlaIII endonuclease per gram of wet cells. When the NlaIII overproducing strain was assayed for NlaIII endonuclease production when grown in noninducing conditions, the cell extract contained only 1000 units per gram of wet uninduced cells. Thus, the induction ratio is 2000-fold. The expression system of the present invention with characteristics of high level of induction and low basal level expression is a very useful expression system for expression of toxic genes such as restriction endonuclease genes in *E. coli*.

Figure 5:
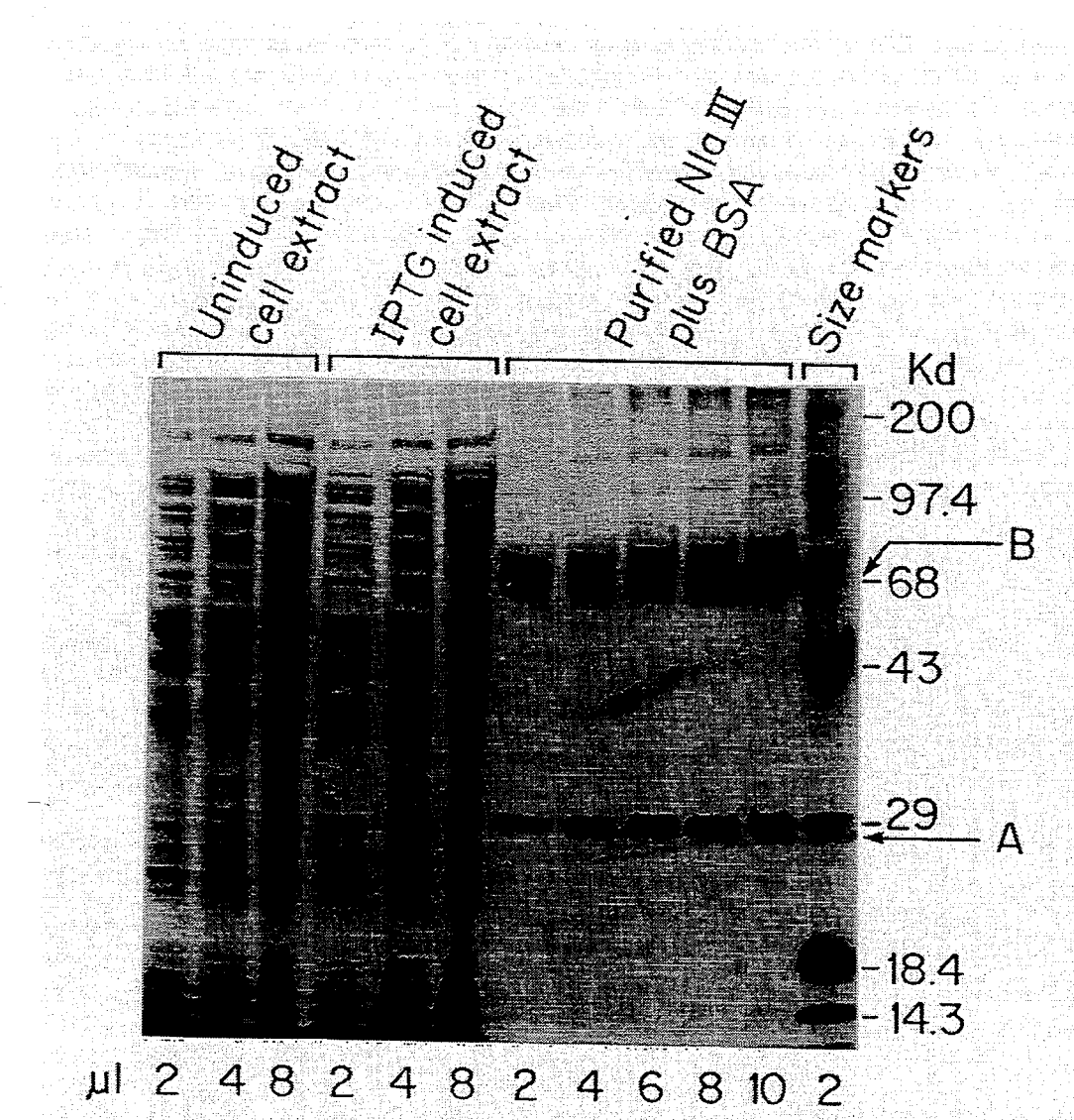
FIG. 5 shows IPTG-induced and uninduced cell extracts and purified NlaIII endonuclease protein. Arrow A and B indicate NlaIII endonuclease protein and bovine serum albumin (BSA), respectively.
Figure 6:
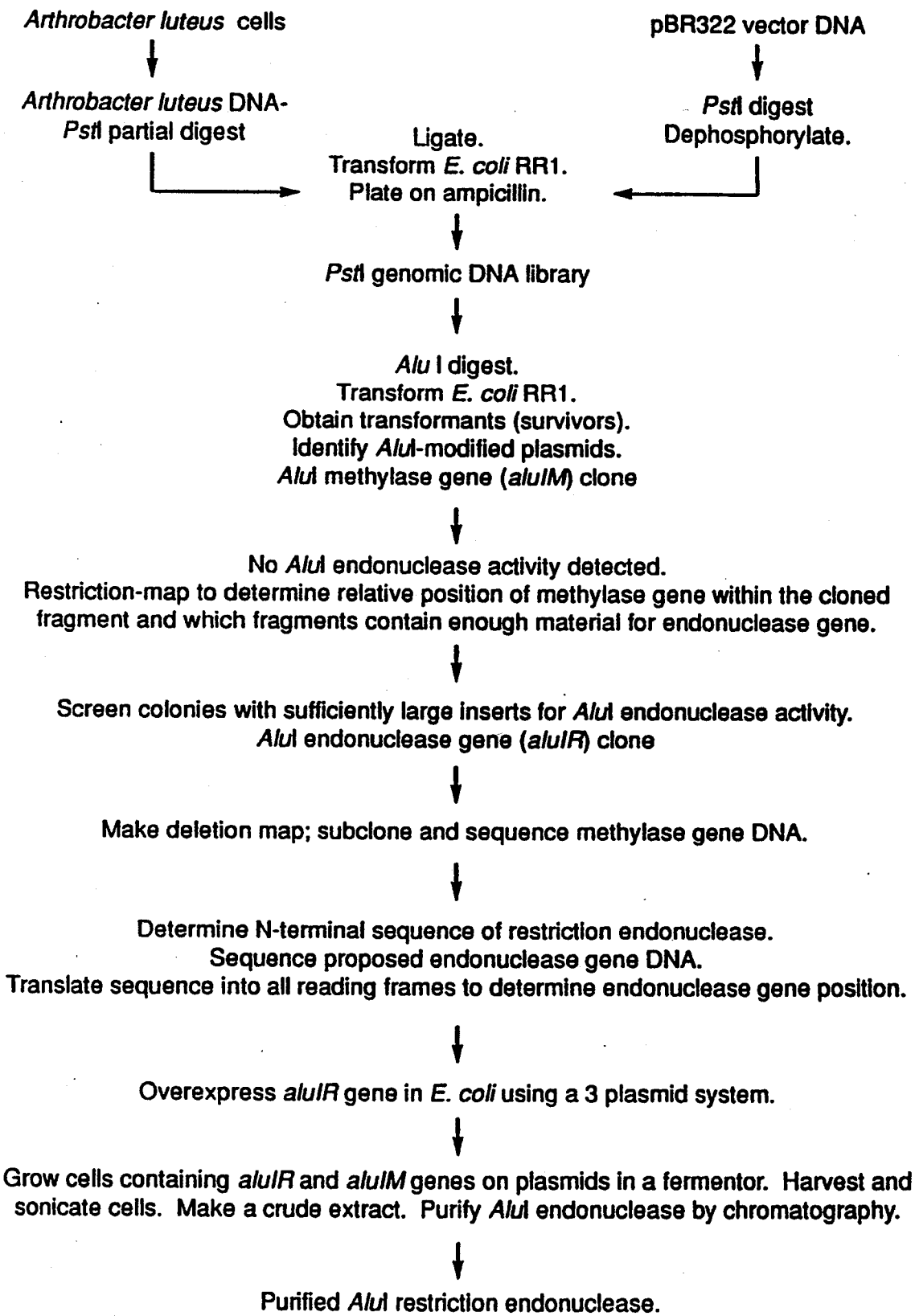
FIG. 6 is a scheme for cloning and producing the AluI restriction endonuclease.

3. Purification of NlaIII endonuclease: Approximately 5 grams of cells from a liter culture were resuspended in 75 ml of sonication buffer (10 mM Tris-HCl, pH 7.8, 10 mM β-mercaptoethanol) and sonicated. The cell debris was removed by centrifugation at 15000×g for 30 minutes and 10 % glycerol was added and supernatant frozen at −70° C. Upon thawing, KCl was added to a final concentration of 0.2M and the cell extract was applied to a phosphocellulose column (2.5×7 cm). A salt gradient was then applied from 0.2M to 2M KCl and fractions collected and analyzed for NlaIII endonuclease activity. Those fractions with NlaIII activity were pooled. After addition of 200 μg/ml of BSA they were loaded onto a hydroxylapatite column equilibrated with a buffer (10 mM KPO4, pH 7, 10 mM β-mercaptoethanol, 0.1 mM EDTA, 0.3M NaCl, 10% glycerol). The enzyme was eluted with a phosphate gradient from 10 mM to 0.7 M KPO4. Fractions containing NlaIII endonuclease were pooled and dialyzed against buffer containing 10 mM Tris-HCl, pH 7.6, 10 mM β-mercaptoethanol, 0.1 mM EDTA, 50 mM NaCl and 10% glycerol. 200 μg/ml of BSA was again added to the enzyme pool which was applied to a DEAE sepharose column (2.5×4.5 cm). The enzyme flowed through and was quickly applied to another hydroxylapatite column. The enzyme was eluted in a phosphate gradient of 10 mM to 0.7M KPO4. The fractions with NlaIII endonuclease were pooled and dialyzed against a storage buffer (10 mM Tris-HCl, pH 7.5, 0.1 mM EDTA, 1 mM dithiothretol, 0.2M KCl, 50% glycerol) and stored at −70° C. A total yield of 400,000 units NlaIII was obtained with the above purification procedure. The purified NlaIII endonuclease was analyzed by SDS-polyacrylamide gel electrophoresis. It was found that the NlaIII endonuclease protein with an apparent molecular weight of 27000 daltons is at least 90% pure (FIG. 5. Note: the 68000 dalton BSA protein is not a contaminating protein. It was added into the NlaIII preparation to stablize the endonuclease).

The NlaIII restriction endonuclease obtained from this purification was substantially pure and free of nonspecific endonuclease and exonuclease. The purity of the NlaIII restriction endonuclease preparation was checked by looking at the following criteria: 1 ) Ligation: After a 20-fold overdigestion of fx DNA with the purified enzyme, greater than 95% of the DNA fragments produced were ligated with T4 DNA ligase. Of these ligated fragments, 95 % could be recut with NlaIII. 2) Prolonged digestion: After incubating a 50 ul reaction containing 1 μg of fx174 DNA and 200 units of enzyme for 16 hours, the same pattern of DNA bands was produced as a reaction performed in one hour with one unit of enzyme. 3) Exonuclease Activity: After incubation of 200 units of enzyme for 4 hours at 37 ° C. in a 50 μl reaction containing 1 μg sonicated $^3$H DNA (105 cpm/μg) 0.21% radioactivity was released. All tests were performed in the following reaction buffer: 50 mM potassium acetate, 20 mM Tris actate, 10 mM magnesium acetate, 1 mM dithiothreitol.

EXAMPLE 3

1. Cloning of a methylase gene into pSYX20 vector: Plasmid pSYX20 is a medium-copy-number plasmid that carries Kan$^r$ and Tc$^r$ genes and a pSC101 replication origin. A methylase gene inserted into the Tc$^r$ gene can be expressed constitutively from the Tc promoter. The construction of pSYX20 has been described in detail in Example 2. Alternatively, any plasmid vector, preferably a medium-copy number, which is compatible with ColEl and μl 5A can be used for cloning of the methylase gene; Bacteriophage vectors can also be used to clone the methylase gene and intergrated into *E. coli* host chromosome for host DNA modification. Two primers with desired restriction sites can be used to amplify the methylase gene from a plasmid or from genomic DNA by the polymerase chain reaction. An efficient ribosome binding site, such as, GGAGGT can be engineered into the primer 7–10 bp upstream of ATG start codon. The polymerase chain reaction conditions are typically 95 ° C. for 1 minute, 50° C. for 2 mintues, 72° C. for 1–2 minutes, 20–30 cycles. The PCR products can be extracted twice with phenol-CHCl3, twice with CHCl3, ethanol-precipitated, and resuspended in TE buffer. After restriction digestion the DNA can be extracted again with phenol-CHCl3 and CHCl3, ethanol-precipitated, dried, and resuspended in TE buffer. The vector DNA pSYX20 is then cleaved with the same restriction endonuclease, extracted with phenol-CHCl3 and CHCl3, and ethanol-precipitated, and resuspended in TE buffer. The DNA containing the methylase gene and the pSYX20 vector DNA can be ligated overnight at 16° C. in a 1X ligation buffer. The ligated DNA can be diluted if necessary by addition of sterile-distilled water and a fraction of DNA can be used to transform *E. coli* cells (mcrA−, mcrBC−, hsd−, mrr−) and plated on Kan (50 μg/ml) plate. Kan$^r$ transformants can be screened for the correct size insert by mini-preparation of plasmid DNA and restriction digestion. The plasmid with the correct size insert can be challenged with the cognate endonuclease to confirm full modification. The methylase gene containing plasmid can be used to transform for example BL21 (λDE3) Δ(hsd-mrr-rncrBC) [pLysS] cells and plated on LB agar plate plus 30 μg/ml of Cm, 50 μg/ml of Kan. Cm$^r$ and Kan$^r$ transformants can be obtained and used later as the host for expression of the corresponding endonuclease. Alternatively, a restriction fragment containing the intact methylase gene can be directly cloned into pSYX20 using restriction sites AatII, EcoRI, ClaI/BspDI, EcoRV, BamHI, SphI, SalI, PshAI, EagI, NruI, BspMI, SmaI, or XhoI.

2. Cloning of restriction endonuclease gene into expression vector pSYX22. Expression vector pSYX22 contains the T7lac promoter, rrnB transcription terminators upstream of T7lac promoter the lacI$^q$ gene, two restriction sites, NdeI and SalI, for translational fusion cloning. The construction of pSYX22 has been described in Example 1. Alternatively, derivative of pSYX22 can be constructed to contain NcoI, SphI, BspHI, or AflIII restriction sites for insert cloning. Two primers can be designed in such a way that the first primer contains an NdeI site which annealed to the start of the endonuclease gene and a SalI site engineered into the second primer which is complementary to the end of the endonuclease gene. The endonuclease gene can be amplified from plasmid clone or genomic DNA by PCR with heat stable DNA polymerase, for example, Vent®, (95° C. for 1 minute, 50° C. for 2 mintues, 72° C. for 1–2 minutes, 20–30 cycles). PCR products can be purified by phenol-CHCl$_3$ and CHCl$_3$ extractions and ethanol-precipitation, and cleaved with NdeI and SalI. The DNA can be again purified by phenol-CHCl$_3$ and CHCl$_3$ extraction and ethanol-precipitation and resuspended in TE buffer. DNA containing the endonuclease gene can be ligated into NdeI/SalI treated pSYX22 at 16° C. overnight. The ligated DNA can be diluted with the addition of sterile-distilled water and a portion of which can be used to transform E. coli cells and plated on Ap plates. Individual transformants can be inoculated into 2 ml of LB plus Ap and shaken overnight at 37° C. Plasmid DNA can be prepared and analyzed by NdeI and SalI restriction digestion. Alternatively, a restriction fragment containing the desired endonuclease gene can be directly cloned downstream of T7lac promoter in the pSYX22 expression vector. Plasmids containing the correct size insert can be used to transform for example BL21 (λDE3) Δ(hsd-mrr-mcrBC) [p(SYX20)Methylase+, pLysS] and plated on LB agar plus Ap (50 µg/ml), Cm (30 µg/ml), Kan (50 µg/ml). E. coli strain BL21 (λDE3) Δ(hsd-mrr-mcrBC)[p(SYX22)R+, p(SYX20)M+, pLysS] can be tested for endonuclease production as follows: 200–1000 ml of rich broth medium plus Ap (50 µg/ml), Cm (30 µg/ml), Kan (50 µg/ml) can be inoculated with 2 ml of overnight cells and shaken at 37° C. to cell density of Klett 75–100. IPTG inducer can be added to the culture to 0.5 mM final concentration. The cells can be induced for 2–14 hours and harvested. Cells can be pelleted by centrifugation at 4° C., 5000×g for 15 minutes, resuspended in sonication buffer (10 mM Tris-HCl, pH 7.8, 10 mM β-mercaptoethanol), and sonicated on ice till complete cell lysis. Cell debris can be removed by centrifugation at 4° C. 15000×g for 30 minutes. The supernatant can be transferred to a new tube and diluted in the sonication buffer and 1–10 µl of the diluted extract can be used to cleave 1 µg of λDNA or any substrate DNA in 1×restriction buffer. After one hour digestion at 37° C. the reaction can be stopped by addition of stop solution and DNA analyzed by agarose gel electrophoresis. Endonuclease yield can be estimated per gram of wet induced cells. The desired restriction endonuclease can be purified by ion exchange columns, gel filtration, or affinity columns. The purified restriction endonuclease can be analyzed by SDS-polyacrylamide gel electrophoresis.

EXAMPLE 4

1. Cloning of the AluI restriction and modification system: The aluIM gene was first cloned on AatII, BamHI, BglII and PstI fragments of *Arthrobacter luteus* genomic DNA in pBR322 digested with the same enzymes and treated with Calf Intestinal Alkaline Phosphatase (CLAP). RR1 and K802 cells were transformed with the ligation mixtures and the transformed cells were plated on ampicillin plates. Survivors were pooled to make a 1° cell pool. DNA from the cell pool was collected to make a 1° plasmid library. Methylase selection was used to identify the aluIM clones by challenging each plasmid library with AluI endonuclease and looking for survivors after transformation. The resulting colonies were pooled to make 2° libraries.

2° libraries were digested with 2 and 8 units of AluI/µg DNA, then analyzed on agarose gels. AluI-resistant, very-high molecular weight subpopulations were seen in the PstI (RR1), BamHI (RR1), BamHI (K802), BglII (RR1) and BglII (K802) libraries but not in the PstI (K802) library. Digestion of the libraries with AluI plus the appropriate cloning enzyme in comparison with digestion by the cloning enzyme alone revealed prominent, AluI-resistant bands in the BamHI and PstI libraries. However, no AluI endonuclease activity was detected.

A 14-kb PstI fragment was transferred from one of the pBR322 clones into pUC19. The resulting transformants were completely resistant to AluI digestion, so the BamHI and PstI libraries were completely remade in pUC19 in the hope that the higher copy number plasmid would provide better methylase protection which would allow the restriction endonuclease to be expressed as well. All of the resulting BamHI and Pst I clones were completely AluI resistant.

2. Restriction mapping of aluIM and aluIR genes: The aluIM and aluIR genes were mapped as follows: The BamHI clones were digested with BamHI. All clones, whether in pBR322 or in pUC19 were found to contain both a 7.4 and a 6.2 kb fragment and some also contained a 5.4 kb piece on one end or a 2.2 kb fragment on the other end. One of the original BamHI clones in pBR322, carrying the 7.4, 6.2, and 5.4 kb fragments was digested with BamHI and religated. 14 Amp$^r$, Tc$^s$ transformants were identified and examined for AluI-resistance and BamHI-fragment composition. All combinations except 7.4+6.2 or all 3 fragments were found. All were AluI sensitive, indicating that both the 6.2 and 7.4 kb fragments are required for AluI methylase activity. The other two smaller fragments were found to be unnecessary for methylase activity, since they mapped to opposite ends of the DNA.

The clone was also mapped with BglII, PstI and ScaI to determine orientation in the vector. BglII was determined to cut 600 bp inside of the BamHI site in the 7.4 kb fragment and 100 bp from the end of the BamHI site in the 6.2 kb fragment, giving a 12.9 kb fragment.

The PstI clones in both vectors all contain a 14.5 kb fragment with or without smaller fragments varying from 2.2 to 6.0 kb. A subclone was made in pUC19 containing one end of the 14 kb fragment. The clone was digested with XbaI in the polylinker and NheI which cuts 5.3 kb from one end of the PstI insert. The plasmid was religated and transformed into RR1 cells. Colonies growing on ampicillin plates were used to make mini-preparations of DNA. Several of the minipreps had the correct structure and were resistant to AluI cleavage, indicating that the methylase gene was located within this 7.2 kb NheI to PstI fragment.

An XmnI subclone was made from the original PstI clone for the purposes of sequencing and locating the endonuclease gene. XmnI cuts 5.1 kb inside one PstI site and 2.3 kb inside the other PstI site, leaving a 6.7 kb fragment containing the methylase and perhaps enough DNA on either end to hold the endonuclease gene. The 6.7 kb XmnI fragment was subcloned into the HincII site in pUC18 and pUC19. The resulting clones were resistant to AluI cleavage in either orientation with respect to the lac promoter, and showed some endonuclease activity.

3. DNA sequence analysis of the aluIM gene: Part of one of the original BamHI clones in pUC and of a Sau-3AI derivative were sequenced (Zhang et al., *Nucleic Acids Research*, 21:905–911 (1993)). A large open reading frame of 1575 bp was found and assigned to the methylase gene. No open reading frame corresponding to the endonuclease gene could be ascertained from the sequence, so the amino terminus of the endonuclease protein was sequenced.

4. Protein sequence analysis of the amino terminus of the aluIR gene: Highly purified AluI endonuclease was prepared in the following manner: 190 g of cells were resuspended in 3 volumes of Buffer A [20 mM KPO$_4$ (pH 7.0), 100 mM NaCl, 10 mM 2-mercaptoethanol, 0.1 mM EDTA] plus 200 µg/ml lysozyme and allowed to sit overnight at 4° C. In the morning, the cells were cracked in the Manton-Gaulin Homogenizer. Cell debris was removed by centrifuging the broken cells at 40,000 rpm for 40 minutes. The following steps were all done at 4° C. NaCl was added to the supernatant to a final concentration of 200 mM before the supernatant was applied to a DEAE sepharose column. At this salt concentration the enzyme flows through this column. Flow-through from the DEAE column was diluted 1:1 with Buffer A at pH 6.8 minus the salt to give a solution with a final NaCl concentration of 100 mM before loading onto a cellulose phosphate column. Enzyme was eluted from the column with a 1.2 l, linear salt gradient from 0.1M to 1.1M NaCl. Gradient fractions were collected and assayed for enzyme on λDNA. Fractions containing enzyme were pooled and dialyzed against 4l of Buffer A at pH 7.2. The dialysate was then loaded onto a heparin sepharose column. The column was rinsed and the enzyme eluted with a linear salt gradient as described for the cellulose phosphate column. Active fractions were again pooled and dialyzed against 10 volumes of Buffer B [20 mM Tris-HCl (pH 7.2), 75 mM NaCl, 10 mM 2-mercaptoethanol, 0.1 mM EDTA and 5% glycerol]. The supernatant was loaded onto a Mono Q column via FPLC. The enzyme was eluted using a linear salt gradient from 50 mM to 600 mM NaCl in Buffer B. Fractions of 1 ml were collected. Enzyme fractions were identified as before, pooled and dialyzed against storage buffer [10 mM Tris-HCl (pH 7.4), 100 mM KCl, 0.1 mM EDTA, 1 mM DTT, 200 µg/ml BSA and 50% glycerol].

The endonuclease was sequenced as follows: The AluI restriction endonuclease was subjected to electrophoresis and electroblotted according to the procedure of Matsudaira (P. Matsudaira, *J. Biol. Chem.*, 262:10035–10038 (1987)), with modifications as previously described (P. A. Waite-Rees et al., *J. Bacteriol.*, 173:5207–5219 (1991); M. C. Loony et al., *Gene*, 80:193–208 (1989)).

The protein sample was subjected to electrophoresis on a Tris-Tribune 10 to 20% polyacrylamide gradient gel (Novel) for three hours and then transferred to a polyvinylidene difluoride (PVDF) membrane (Problott, Applied Biosystems Inc.) using 10 mM CAPS buffer (10 mM 3-[cyclohexylamino]-1-propanesulfonic acid, 10% methanol, 0.05% SDS, 0.005% dithiothreitiol, adjusted to pH 11.0 with NaOH) for 18 hours at 200 volts in a tank electroblotter (TE52, Hoeffer). The membrane was stained with Coomassie blue R-250 and a band of approximately 38 kd (15 mg) was excised and subjected to sequential degradation (P. A. Waite-Rees et al., *J. Bacteriol.*, 173:5207–5219 (1991)). The first 24 residues of the 38 kd protein corresponded to Gly—Ser—Ile—Val—Val—Asp—Gln—Ile—Gly—Pro—Asp—Gly—Glu—Leu—Val—Pro—Asp—Val—Asp—Leu—Thr—Leu—Ser—Glu and residues 21 and 23 (Thr and Ser) were somewhat ambiguous.

5. DNA sequence analysis of aluIR gene: The ends of the XmnI subclone were sequenced by thermocycle sequencing using Vent® DNA Polymerase (New England Biolabs, Beverly, Mass.) and primers corresponding to the polylinker of pUC. Twenty cycles of sequencing were performed, each consisting of 20 seconds at 95° C., 20 seconds at 55° C. and 20 seconds at 70° C. The sequence was read, and new primers were synthesized from the sequence and used to extend each sequence further. This was repeated a third time, generating a total of 640 nucleotides of sequence from each end. These sequences were translated in all six reading frames, and these hypothetical sequences were compared to the known sequence of the amino terminus of the endonuclease to determine if any of this sequenced DNA encoded the beginning of the enzyme. A perfect match was found in one of the forward reading frames upstream of, and oriented in the same direction as, the methylase gene. This indicated that the endonuclease gene started approximately 100 base pairs downstream of the XmnI site, approximately 2 kb from the start of the methylase gene.

4. Overexpression of the aluIR and aluIM genes in *E. coli*:

A. Expression of the aluIR and aluIM genes under the λP$_L$promoter: Several different subclones were made in which portions of the BamHI or PstI inserts were cut out and ligated behind the λP$_L$ promoter in pGW7. Plasmid GW7 (constructed by Geoffrey Wilson at New England Biolabs) is a derivative of pBR322 in which the beginning of the tetracycline resistance gene has been replaced by the regulatory region of phage λ. pGW7 contains the cI gene with a temperature-sensitive mutation. At low temperature, the cI repressor is active and transcription from the P$_L$ promoter is inhibited. At high temperature, however, the repressor is inactive and transcription from P$_L$ is constitutive. A 12.8 kb BglII fragment from the smallest BamHI clone was ligated into BarnHI-digested, BAP-treated pGW7. Similarly, the smallest PstI clones were digested with EcoRI (cuts in the polylinker) and BglII (cuts just inside of one of the PstI sites). The fragment containing the AluI DNA was ligated to an EcoRI to BamHI fragment of pGW7 containing the P$_L$promoter. The ligation mixtures were transformed into RR1 cells and selected on ampicillin plates. Minipreparations of the resulting colonies were analyzed for the proper construct and AluI resistance.

One of the PstI subclones and 3 of the BamHI subclones with the correct structure were chosen to assay for endonuclease activity. These subclones were grown in LB at 30° C. to an O.D.$_{600}$ of 0.8 and then the temperature was shifted to 43° C. Cultures were grown for an additional 3 hours, then collected by centrifugation. The cell pellet was resuspended in sonication buffer (20 mM Tris-Cl, pH 7.5, 10 mM 2-mercaptoethanol, 50 mM NaCl, and 0.1 mM EDTA) plus 0.1 µg/ml lysozyme and frozen overnight. Cells were broken in the morning and assayed for AluI activity. None was found.

B. Expression of the aluIM and aluIR genes in pUC: According to the restriction mapping digestions, the 6.7 kb XmnI fragment in the PstI clones which has the methylase gene in the center has room for the endonuclease on either side. The smallest PstI clone was digested with XmnI for 90 minutes. The fragment was gel-purified and ligated into HincII-cut, CIAP-treated pUC19. Attempts were made to reverse the clone by digesting the insert with BamHI and PstI which cut outside of the insert, in the polylinker. This fragment was inserted into BamHI- and PstI-cut pUC18. The inserts in all of the transformants in pUC19 and pUC18 were mapped by restriction digestion and all were shown to have the methylase gene running against the lac promoter. None of the clones had any detectable endonuclease activity. The methylase gene was then cloned alone into pUC19. The gene was amplified by polymerase chain reaction (30 cycles of 90 seconds at 95° C., 90 seconds at 55° C., 90 seconds at 72° C.) using Vent®️ DNA Polymerase and primers synthesized using the sequence of the ends of the methylase gene. The primers introduced a KpnI site at one end and a PstI site at the other end of the product. The 1.4 kb product was purified away from primers and dNTPs by gel electrophoresis and was digested with 20 units of PstI and 20 units of KpnI at 37° C. [in 10 mM Bis Tris Propane-HCl, 10 mM MgCl$_2$, 1 mM DTT (pH 7.0 at 25° C.)]. The fragment was purified away from restriction enzymes and ends by extraction with phenol:CHCl$_3$ and precipitated with ethanol, and then ligated into PstI- and KpnI-digested pUC19. Resulting transformants were fully protected against AluI digestion. Competent cells were made with this construct in *E. coli* ER2267. Another attempt was made to reverse the XmnI insert in pUC 18. The BamHI to PstI fragment containing the XmnI insert was ligated into BamHI, PstI digested pUC18. The ligation mixture was transformed into cells containing the AluI methylase on pUC 19.

One of the AluI resistant transformants was assayed for endonuclease activity. A 100 ml culture of cells from a single colony was centrifuged. The pellet was resuspended in 3 ml of sonication buffer and sonicated. 7.5 µl of the crude solution was added to a tube containing 7.5 µg of λDNA in AluI buffer in a volume of 150 µl. Several 2-fold serial dilutions were made. The assay tubes were incubated at 37° C. for 1 hour. The reactions were stopped by the addition of Stop Dye containing 50% glycerol, 50 mM EDTA and 0.25% Bromophenolblue and then electrophoresed on an agarose gel, along with a similar series of dilutions of purified AluI on λDNA. The cells contained approximately 40,000 units of AluI endonuclease per liter of culture.

C. Expression of the aluIM gene in a low copy-number plasmid: Since the methylase gene on pUC19 is not compatible with overexpression of the endonuclease gene on pUC18 (both plasmids contain the same origin of replication and thus will compete for presence in the cell), the methylase gene was moved onto pACYC184, which contains the µl 5a origin of replication. The same KpnI to PstI fragment containing the methylase gene as in B above was swapped for the XbaIM gene in pBZXbaIM300-5. This is a pACYC184-based plasmid with the XbaI methylase gene cloned in the middle of the tet gene, under the lac promoter. It has been modified to contain a good ribosome binding site as well.

Chloramphenicol resistant transformants with the correct size insert were tested for activity in the following way: 100 ml of LB was inoculated with a single colony and grown overnight with shaking at 37° C. The cells were collected by centrifugation and the pellet resuspended in 3 ml of sonication buffer. Lysozyme was added to 0.14 mg/ml and the cells were incubated on ice for 1 hour. A 1 ml portion of the mixture was sonicated at microtip setting 2.5, 90% duty for 4×10 second bursts. Four µl of the crude supernatant were added to a tube containing 20 µl of protection buffer [50 µg/ml λDNA, 106 µM s-adenosyl methionine and 1X M.AluI buffer (50 mM Tris-Cl (pH 7.5), 10 mM EDTA, 5 mM 2-mercaptoethanol)]. Four 2-fold serial dilutions were made in the same buffer. The 10 µl reactions were incubated at 37° C. for 1 hour and the enzyme was heat-killed at 65° C. for 10 minutes. The methylated DNA was then challenged with AluI endonuclease in a 50 µl reaction volume in 1X AluI endonuclease buffer containing MgCl$_2$ and AluI endonuclease at final concentrations of 30 mM and 8 units/reaction, respectively. The methylated DNA was challenged for 30 minutes at 37° C., and then the reactions were run on an agarose gel. The DNA appeared to be completely methylated.

D. Expression of the aluIM gene in a medium copy-number plasmid which is compatible with ColE1 and µl 5A: The methylase gene was next moved into a pSC101-based plasmid with a mutated copy number, in an attempt to get better expression of the methylase, as it was hoped that better protection of the cells would permit overexpression of the endonuclease. Having the methylase on a pSC101-based plasmid would also allow subcloning of the endonuclease in the T7 expression system, since the system requires the presence of pACYC-based pLysS to reduce the basal level of expression of certain toxic genes. The methylase gene on a pACYC-based plasmid would compete with pLysS, and the methylase on a ColE1 plasmid would compete with the endonuclease on the T7 vector.

Plasmid pSYX20 (created by Shuang-yong Xu, New England Biolabs) is a medium-copy-number plasmid that carries Kan$^r$ and Tc$^r$ genes and a pSC101 replication origin. A gene inserted into the Tc$^r$ gene can be expressed constitutively from the Tc promoter. Such an insertion in the unique EcoRV, BamHI, SalI and SphI restriction sites inactivates the Tc$^r$ gene, which provides an easy screening method for detection of the insert.

The aluIM gene was excised from pBZ.AluIM300-1 CsCl-purified DNA by digestion with KpnI for 1 hour at 37° C., followed by digestion with PstI at 37° C. for 1 hour. The resulting 3′ overhanging ends were chewed back to leave blunt ends using T4 DNA Polymerase plus 25 µM dNTPs at 37° C. for 5 minutes. The polymerase was heat-inactivated at 75° C. for 10 minutes, and the methylase-containing DNA fragment was purified away from the vector DNA and dNTPs by electrophoresis on an 0.7% GTG agarose gel (FMC Bioproducts, Rockland, Me. 04841) in TBE buffer (0.089M Tris-Borate, 0.089 M boric acid, 0.002M EDTA) plus 0.5 µg/ml ethidium bromide, and eluted from the gel in an Elutrap Electro-Separation Chamber (Schleicher and Schuell, Keene, N.H. 03431, available from American Bioanalytical, Natick, Mass. 01760). The fragment was then precipitated with ethanol and the DNA was resuspended in 30 μl of TE.

The vector, pSYX20, was prepared by digestion with EcoRV (which leaves blunt ends) at 37° C. for 1 hour, followed by treatment with CIAP at 50° C. for 1 hour to prevent self-ligation of the vector. The CIAP was inactivated by adding 10 mM EDTA and heating the reaction at 70° C. for 10 minutes, followed by 2 extractions with equal volumes of phenol:CHCl$_3$, 2 extractions with CHCl$_3$, and precipitation with ethanol. The alulM gene was then ligated into the linearized, CIAP-treated pSYX20.

One hundred μl of competent RR1 cells were transformed with 3 μl of the ligation mixture. The cells and DNA were incubated on ice for 5 minutes, heat shocked at 37° C. for 1 minute and returned to ice for 15 minutes. After the addition of 0.4 ml of LB to the mixture, it was incubated at 37° C. for 50 minutes to allow the cells to express the kan$^r$ gene before selection. Two hundred μl of the transformation mix was plated on LB plates containing 50 μg/ml kanamycin.

Overnight cultures of 12 of the 16 resulting transformants were inoculated in 2 ml of LB plus 50 μg/ml kanamycin. The cultures were incubated at 37° C. with shaking. In the morning, plasmid DNA was collected from the cultures using a modification of the boiling minipreparation procedure (*Molecular cloning*, Maniatis, Fritsch and Sambrook, Cold Spring Harbor, 366-367 (1982)). 1.5 ml of each culture was transferred to a separate microcentrifuge tube and centrifuged at 8000 rpm in an Eppendorf microcentrifuge for 1 minute. The supernatants were aspirated off and the pellets were resuspended in 0.35 ml of 10 mM Tris-HCl (pH 7.5), 50 mM EDTA, 8% (w/v) sucrose and 0.5% (v/v) Triton X-100). Twenty-five μl of 5 mg/ml lysozyme, dissolved in the same solution, was added to each tube. The tubes were placed in a boiling water bath for 40 seconds and then centrifuged for 10 minutes at 14,000 rpm. Viscous pellets containing cell debris and chromosomal DNA were removed using sterile toothpicks. The supernatants were extracted with an equal volume of phenol:CHCl$_3$ and centrifuged for 6 minutes at 14,000 rpm. The aqueous phases were precipitated with 0.3M NaOAc and 0.6 volumes of isopropanol and then were centrifuged for 15 minutes at 14,000 rpm at room temperature. The supernatants were aspirated off and the pellets were allowed to dry at room temperature. The dried pellets were resuspended in 37.5 μl of TE. An aliquot of 12.5 μl of RNase A (4 μg/ml) was added to each tube.

2.5 μl aliquots of the DNA samples were digested with AluI. Of the 12 samples, 3 were completely resistant to cleavage by AluI. Those 3 samples were subsequently digested with HindIII, which is blocked by AluI methylation. All 3 clones were also protected against digestion with HindIII. One of the 3 clones, named pCDM9, was used to make competent RR1 and RR1(λDE3)/pLysS cells to aid in further endonuclease subcloning steps.

E. Expression of the alulR gene under P$_{tac}$ promoter: Since the methylase/endonuclease construct in pUC18 produced a fusion with a partial lacZ gene product, and did not produce as great a yield of endonuclease as was desired, the alulR gene was subcloned in pAGR3 under the P$_{tac}$ promoter. Plasmid pAGR3 was constructed by William Jack at New England Biolabs. It is a pBR322-based expression vector, containing the P$_{tac}$ promoter followed by an NcoI site and a BamHI site. Since NcoI contains the sequence ATG within its recognition site, any gene with an NcoI site at its initiation codon can be subcloned against the promoter, presumably for optimal expression. The vector also encodes the lacI$^q$ gene, whose product acts as a repressor, binding to the P$_{tac}$ promoter. Transcription of the gene behind the P$_{tac}$ promoter is thus repressed while the cells are growing until IPTG is added. IPTG binds to the lac repressor and causes it to unbind from the P$_{tac}$ promoter, allowing transcription to proceed.

An NcoI site was introduced at the initiation codon of the alulR gene by amplifying the gene using the polymerase chain reaction (R. K. Saiki et al., Science, 230:1350-1354 (1985)) with a primer corresponding to the start of the gene. The primer (5' GAA CAG ACC, ATG GGA TCA ATC GTC GTT GAC 3', SEQ ID: 15) introduces an NcoI site at the ATG codon. It also introduces two extra nucleotides 5' to the NcoI site. Since the carboxyl terminus of the restriction endonuclease had not been sequenced, the primer for the 3'-end of the PCR reaction was one corresponding to the amino terminus of the methylase gene, which had been sequenced. Primer 2 (5' GCA ATG GAT CC G AAT TCC TCT GAA GCT TGA CAG CTC 3', SEQ ID: 16) introduces an EcoRI and a BamHI site for ease of subcloning the complete alulR gene. This region also contains two AluI sites.

The alulR gene was amplified by PCR reaction with Vent ® DNA polymerase (95° C. for 1 minute, 50° C. for 0.5 minute, 72° C. for 2 minutes, for 15 cycles). The DNA products were extracted twice with an equal volume of phenol:CHCl$_3$ and twice with an equal volume of CHCl$_3$ and precipitated with ethanol. After restriction digestion with BamHI and NcoI for 90 minutes at 37° C., the DNA fragment containing the endonuclease gene was purified away from primers, ends and dNTPs by electrophoresis in 0.7% GTG agarose and eluted from the gel in an Elutrap Electro-Separation Chamber. The fragment was ethanol-precipitated and resuspended in 20 μl of TE buffer.

The alulR gene was ligated behind the P$_{tac}$ promoter in BamHI/NcoI cleaved pAGR3 and transformed into RR1 cells. Five μl of the ligation mix was added to a tube containing 100 μl of competent cells. The mixture was incubated on ice for 5 minutes, heat shocked at 37° C. for 1 minute and returned to ice for 15 minutes. After addition of 0.4 ml of Luria Broth (LB) to the ligation mixture, 100 μl of that mixture was plated on LB plates containing 100 μg/ml ampicillin. The plates were incubated overnight at 37° C. to allow the transformed cells to grow into colonies.

To determine which colonies had the appropriate insert, minipreparations of DNA were made from 12 colonies. Aliquots of 4 μl of the DNA samples were digested with BamHI and NcoI for 1 hour at 37° C. Stop Dye was added to each reaction and the reactions were electrophoresed on a 1.0% agarose gel. Two sizes of insert were revealed, and one or two of each category were chosen to assay for activity.

To test for activity, RR1 cells with or without the methylase on pACYC or pSX20 were transformed with DNA from the chosen minipreps. The transformed cells were again plated on ampicillin plates and allowed to grow overnight. Tubes containing 2 ml of LB plus the appropriate antibiotics (in this case, ampicillin) were again inoculated with single colonies resulting from the transformation event. These cultures were incubated overnight at 37° C. with shaking.

In the morning, the cultures were diluted 1:49 or 1:99 into fresh LB plus antibiotics, and grown at 37° C. to a Klett reading of 100. The endonuclease gene was then induced by the addition of IPTG to a final concentration of 0.3 mM and the cultures were agitated at 37° C. for an additional 2 hours. The cells were harvested by centrifugation at 5,000 rpm for 10 minutes. The cell pellets were resuspended in 0.1 volume of 10 mM Tris, 1 mM EDTA, 10 mM 2-mercaptoethanol. Lysozyme was added to 0.15 mg/ml, and the cells were broken by sonication. The broken cells were centrifuged at 14,000 rpm in an Eppendorf microcentrifuge for 6 minutes and the resulting supernatant was assayed for AluI activity on λDNA.

No activity was detected in cells with the endonuclease under the $P_{tac}$ promoter in the absence of the AluI methylase, nor was any activity detected in the presence of pBZ.AluIM300-1. In cells containing the endonuclease as well as the methylase on pCDM9, however, one colony out of four showed activity, giving 182,000 units/g of wet cells or 4,000,000 units/l of culture. The colony showing activity was named pCDG103.

F. Expression of the aluIR gene in a medium-copy number plasmid under the T7lac promoter: The aluIR gene was inserted into pBPA 1 in parallel with pAGR3. pBPA 1 is derived from pET 11 c which is a T7 expression vector derived from pBR322 that contains a lac operator 4 bp down stream of the T7 promoter (this T7 promoter plus lac operator is called T7lac promoter), the lacI$^q$ gene, and two restriction sites, NdeI and BamHI, for cloning (Dubendorff and Studier, *J. Mol. Biol.*, 219:45-59 (1991)). A pET-11c derivative, pAII17 (Kong et al., *J. Biol Chem.*, 268:1965-1975 (1993)), was constructed containing four copies of the rrnB transcription terminator upstream of the T7 promoter. The transcription terminators further decrease the basal level of expression of the target gene. The NdeI site in pAII17 was changed to an NcoI site by swapping a BamHI to XbaI fragment from pET3d with that fragment in pAII17.

The same purified NcoI to BamHI fragment containing the aluIR gene as in C above was inserted into pBPA 1 digested with NcoI and BamHI. RR1 cells were again transformed with several µl of the ligation mixture and plated on ampicillin plates. Minipreparations of DNA were made from 19 colonies resulting from the transformation. Of these, two sizes of inserts were found. Several examples of each size of insert were chosen for further investigation. The DNA from these samples was transformed into RR1 (DE3)/pLysS cells. These cells contain the T7 RNA Polymerase gene as a λ lysogen on the chromosome, under the lacUV5 promoter. Plasmid pLysS is a pACYC-based plasmid encoding phage T7 lysozyme (which inhibits T7 RNA Polymerase) to reduce the basal level target gene expression from the T7lac promoter (Studier, *J. Mol. Biol.*, 219:37-44 (1991)).

Once again, no activity was observed in cells containing the endonuclease under the T7lac promoter in the absence of AluI methylase or in the presence of pBZ.AluIM300-1. Four transformants were chosen from RR1 (DE3)pLysS cells which contained the methylase on pCDM9 and the endonuclease under T7 control. These were chosen at random, without restriction analysis of the plasmids, since the presence of three plasmids in a cell makes restriction analysis very difficult. In the presence of pCDM9, 4 out of 4 colonies showed appreciable amounts of AluI endonuclease activity upon induction with IPTG. The activity ranged from 91,000 units/g of wet cells to 364,000 units/g. This corresponds to 2,000,000 to 8,000,000 units/l of culture. The plasmid producing the highest endonuclease yield was named pCDH104. This plasmid was transformed into RR1 (DE3)/pLysS/pCDM9 cells. An isolate from this transformation was selected and designated NEB 848, a sample of which has been deposited at the American Type Culture Collection, 12301 Parklawn Drive, Rockville, Md. 20852, on Aug. 24, 1993 and has received accession no. 69394.

5. Assay for AluI endonuclease activity: Cells transformed with pCDG 103 or pCDH104 were assayed for activity in the following manner: A single colony from a transformation reaction was inoculated into 2 ml of LB or Rich Broth (RB) plus the appropriate antibiotics (100 µg/ml Ap for pCDG 103 or pCDH 104, 50 µg/ml Kan for pCDM9 and 30 µg/ml Cm for pLysS, if present). The cultures were grown overnight at 37° C. with agitation. Approximately 1 ml of overnight culture was transferred to 100 ml of fresh LB or RB supplemented with the appropriate antibiotics. The cultures were allowed to grow at 37° C. with shaking until they reached mid-log phase, at a Klett of 100 units. The cells were then induced by the addition of IPTG to a final concentration of 0.3 mM. The cells were incubated at 37° C. with shaking for another 2 to 4 hours. At this point, the cells were collected by centrifugation at 5000 rpm for 10 minutes at 4° C. The supernatants were decanted and the pellets were frozen at −20° C. The following day, the pellets were resuspended in 0.1 volume of TE plus 10 mM 2-mercaptoethanol and lysozyme was added to 0.15 µg/ml. The cells were sonicated four times for 15 seconds each at a microtip setting of 5, 90% duty, continuous bursts and ~22 watts. One ml of the sonicated crude solution was transferred to an Eppendorf tube and the cell debris was pelleted at 14,000 rpm for 6 minutes, at 4° C. The resulting supernatant was assayed for endonuclease activity as follows: 1 µl of supernatant was transferred to a microtiter plate well containing 1 µg of λDNA in a total volume of 50 µl, in 1X NEBuffer #1[10 mM Bis Tris Propane-HCl, 10 mM MgCl$_2$, 1 mM DTT (pH 7.0 at 25° C.)] and 100 µg/ml BSA. 10 µl from this well was transferred into the next well containing 40 µl of the λDNA/NEBuffer #1 solution; in turn, 25 µl from the second well was transferred to the third well containing 25 µl of λDNA/NEBuffer #1 solution. Several more 2-fold serial dilutions (25 µl into 25 µl) were made. The wells were covered with tape and the whole microtiter dish was incubated in a 37° C. incubator for 1 hour. At the end of an hour, the reactions were stopped by the addition of one-sixth volume of Stop Dye. Twenty-five µl of the reactions were run on a 1.0% agarose gel made up in TBE buffer. A unit of AluI was defined as the amount of enzyme required to cleave 1 µg of λDNA to completion in a 50 µl volume in 1 hour at 37° C. When the amount of AluI present is insufficient to cleave all of the sites in I, larger bands become visible on the gel, when viewed under UV light. Thus, the titer of the enzyme is based on the last lane in which no partial bands are observed. Typically, pCDH104 produces 300,000 units/g of wet cells or more (4,000,000–8,000,000 units/liter of culture)in RR1 (DE3)/pLysS/pCDM9 cells.

6. Stability test: RR1(DE3)/pLysS/pCDM9/pCDH104 cells were frozen in 25% glycerol at −70° C. overnight. Cells were streaked out on LB agar plus Ap, Cm, and Kan from the frozen stock to obtain a single colony. 500 ml of fermentation rich broth plus antibiotics was inoculated with a single colony and shaken overnight at 30° C. Because the cells were very sparse at this point, they were not diluted but were allowed to continue to grow, with shaking, at 37° C. until they reached a Klett of 200, at which point a sample was saved, and the rest of the culture was induced by the addition of IPTG to 0.3 mM to test for endonuclease activity. While the culture was being induced, the pre-induction sample was tested for retention of the endonuclease plasmid. The sample was diluted and plated on LB agar plates or LB plates supplemented with 100 μg/ml Ap. It was found that the overproducing strain had 80% of the plating efficiency on ampicillin plates as on non-selective plates ($1.5 \times 10^9$ colony forming units/ml). The induced culture was harvested after 4 hours. Cells were recovered by centrifugation at 5,000 rpm for 10 minutes at 4° C. A cell extract was prepared and AluI endonuclease activity determined on λDNA. At least $5 \times 10^5$ units of AluI endonuclease/gram of wet cells were detected.

7. Purification of AluI restriction endonuclease from AluI overproducer strain (NEB #848). Purification Protocol: 100 l of rich broth plus 100 μg/ml Ap, 30 μg/ml Cm and 50 μg/ml Kan were inoculated with 3 l of an overnight culture of RR1 (DE3) cells containing the T7 lysozyme gene on pLysS, the AluI methylase on pCDM9 and the AluI endonuclease on pCDH104. The cells were aerated at 37° C. until they reached a Klett of 192. The cells were induced with IPTG to a final concentration of 0.4 mM, then allowed to grow for 4 hours. The cells were collected by running the fermentation through a Sharples centrifuge at 17,000 rpm for 60 minutes. The cell pellet was frozen at −70° C. 50 g of cells were cracked in the Manton-Gaulin Homogenizer in 3 volumes of Buffer C [20 mM KPO$_4$ (pH 7.2), 100 mM NaCl, 10 mM 2-mercaptoethanol, 0.1 mM EDTA and 5% glycerol]. Cell debris was removed by centrifuging the broken cells at 40,000 rpm for 40 minutes. The following steps were all done at 4° C. NaCl was added to the supernatant to a final concentration of 250 mM before the supernatant was applied to a 5×10 cm DEAE sepharose column equilibrated with Buffer D [20 mM KPO$_4$ (pH 7.2), 250 mM NaCl, 10 mM 2-mercaptoethanol, 0.1 mM EDTA and 5% glycerol]. At this salt concentration the enzyme flows through this column. Flow-through from the DEAE column was diluted 1:1 with Buffer E [20 mM KPO$_4$ (pH 6.9), 100 mM NaCl and 10 mM 2-mercaptoethanol, 0.1 mM EDTA and 5% glycerol] minus the salt to give a solution with a final NaCl concentration of 125 mM before loading onto a 5×15 cm cellulose phosphate column equilibrated with Buffer E. After loading, the column was rinsed with one volume of Buffer E. Enzyme was eluted from the column with a 2 l, linear salt gradient from 0.1M to 1 M NaCl. 20 ml fractions were collected and assayed for enzyme on λDNA. Fractions containing enzyme were pooled and dialyzed overnight against 10 volumes of Buffer E. The dialysate was then loaded onto a 2.6×10 cm heparin sepharose column equilibrated with Buffer E. The column was rinsed and the enzyme eluted with a linear salt gradient as described for the cellulose phosphate column. Active fractions were again pooled and dialyzed against 10 volumes of Buffer B [20 mM Tris-HCl (pH 7.2), 75 mM NaCl, 10 mM 2-mercaptoethanol, 0.1 mM EDTA and 5% glycerol]. The dialysate was centrifuged at 10,000 rpm to eliminate any precipitate which formed during the dialysis. The supernatant was loaded onto a Mono Q column via FPLC. The enzyme solution was loaded at 0.5 ml/min and eluted using a linear salt gradient from 50 mM to 600 mM NaCl in Buffer B. Fractions of 1 ml were collected into tubes containing 100 μg BSA in 0.5 ml of Buffer B to prevent the enzyme from sticking to the walls of the tubes. AluI generally elutes from Mono Q at 200 mM salt. Enzyme fractions were identified as before, pooled and dialyzed against storage buffer [10 mM Tris-HCl (pH 7.4), 100 mM KCl, 0.1 mM EDTA, 1 mM DDT, 200 μg/ml BSA and 50% glycerol]. The dialyzed, purified enzyme was stored at −20° C.

Assay of AluI activity in the crude showed 700,000 units/g of cells. Out of 34,000,000 units in 50 grams of cells, the final yield was 150,000 units of AluI endonuclease, or 0.44% of the enzyme in the crude supernatant.

The AluI restriction endonuclease obtained from this purification was substantially pure and free of non-specific endonuclease and exonuclease. The purity of the AluI restriction endonuclease preparation was checked by looking at the following criteria: (1) Ligation: After a 10-fold overdigestion of λDNA, greater than 95% of the DNA fragments produced were ligated with T4 DNA Ligase. Of the ligated fragments, 95% could be recut with AluI. 2) Prolonged digestion: After incubating a 50 μl reaction containing 1 μg of λDNA and 50 units of enzyme for 16 hours, the same pattern of DNA bands was produced as a reaction performed in one hour with one unit of enzyme. 3) Exonuclease Activity: After incubation of 100 units of enzyme for 4 hours at 37° C. in a 50 μl reaction containing 1 μg sonicated $^3$H DNA ($10^5$ cpm/μg) less than 0.3% radioactivity was released. All tests were performed in the following reaction buffer: 10 mM Bis Tris Propane-HCl, 10 mM MgCl$_2$, 1 mM dithiothreitol (pH 7.0 at 25° C.).

---

What is claimed is:

1. Isolated DNA coding for restriction endonuclease, wherein the isolated DNA is obtainable from the plasmid p(UC)AatIIR+M+18.

2. A recombinant vector containing DNA coding for AatII restriction endonuclease.

3. The isolated DNA of claim 1 coding for AatII endonuclease and methylase, wherein the isolated DNA is obtainable from the plasmid p(UC)AatIIR+M+18.

4. A host cell transformed with the recombinant vector of claim 2.

5. A method of producing AatII restriction endonuclease comprising culturing a host cell transformed with the vector of claim 2 under conditions suitable for expression of AatII and recovering AatII.

* * * * *

UNITED STATES PATENT AND TRADEMARK OFFICE
CERTIFICATE OF CORRECTION

Page 1 of 13

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

Column 5, line 26    replace "Plac" with --$P_{lac}$--

Column 5, line 26    replace "PlacUV5" with --$P_{lacUV5}$--

Column 5, line 26    replace "Ptac" with --$P_{tac}$--

Column 5, line 26    replace "λPL" with --$\lambda P_L$--

Column 17, line 39   replace "lacZa" with --lacZα--

Column 20, line 9,   replace "fx" with --Φx--

UNITED STATES PATENT AND TRADEMARK OFFICE
CERTIFICATE OF CORRECTION

Page 2 of 13

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

```
Column 1, line 18     replace "Alul" with --AluI--
Column 4, line 21     replace "aatllR" with --aatIIR--
Column 4, line 21     replace "aatllM" with --aatIIM--
Column 4, line 21     replace "aatllR" with --aatIIR--
Column 4, line 22     replace "aatllM" with --aatIIM--
Column 4, line 24     replace "aatllR" with --aatIIR--
Column 4, line 24     replace "aatllM" with --aatIIM--
Column 4, line 25     replace "aatllR" with --aatIIR--
Column 4, line 25     replace "aatllM" with --aatIIM--
Column 4, line 48     replace "alulR" with --aluIR--
Column 4, line 48     replace "alulM" with --aluIM--
Column 4, line 49     replace "alulR" with --aluIR--
Column 4, line 49     replace "alulM" with --aluIM--
Column 4, line 51     replace "alulR" with --aluIR--
```

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

Column 4, line 51    replace "alulM" with --aluIM--

Column 4, line 52    replace "alulR" with --aluIR--

Column 4, line 52    replace "alulM" with --aluIM--

Column 4, line 58    replace "aatllM" with --aatIIM--

Column 4, line 60    replace "aatllR" with --aatIIR--

Column 6, line 44    replace "AatlIM18" with --AatIIM18--

Column 7, line 10    replace "aatllR" with --aatIIR--

Column 7, line 10    replace "aatllM" with --aatIIM--

Column 7, line 21    replace "aatllM" with --aatIIM--

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

| | | |
|---|---|---|
| Column 7, line 23 | replace "aatllM" with | --aatIIM-- |
| Column 7, line 44 | replace "aatllR" with | --aatIIR-- |
| Column 7, line 44 | replace "aatllM" with | --aatIIM-- |
| Column 9, line 11 | replace "Alul" with | --AluI-- |
| Column 9, line 12 | replace "alulM" with | --aluIM-- |
| Column 9, line 18 | replace "alulR" with | --aluIR-- |
| Column 9, line 28 | replace "alulM" with | --aluIM-- |
| Column 9, line 45 | replace "Plac" with | --$P_{lac}$-- |
| Column 9, line 45 | replace "PlacUV5" with | --$P_{lacUV5}$-- |
| Column 9, line 45 | replace "Ptac" with | --$P_{tac}$-- |
| Column 9, line 45 | replace "PR" with | --$P_R$-- |
| Column 9, line 46 | replace "IPL" with | --$\lambda P_L$-- |
| Column 10, line 12 | replace "aatllM" with | --aatIIM-- |

UNITED STATES PATENT AND TRADEMARK OFFICE
CERTIFICATE OF CORRECTION

PATENT NO. : 5,405,768  
DATED : April 11, 1995  
INVENTOR(S) : Shuang-yong Xu, et al.

Page 5 of 13

It is certified that error appears in the above-indentified patent and that said Letters Patent is hereby corrected as shown below:

Column 10, line 19   replace "aat11M" with --aatIIM--

Column 10, line 20   replace "aat11R" with --aatIIR--

Column 10, line 21   replace "aat11M" with --aatIIM--

Column 10, line 23   replace "Aat1IR" with --AatIIR--

Column 10, line 25   replace "Aat1IR" with --AatIIR--

Column 10, line 27   replace "aat11M" with --aatIIM--

Column 10, line 27   replace "aat11R" with --aatIIR--

Column 10, line 28   replace "aat11M" with --aatIIM--

Column 10, line 28   replace "aat11R" with --aatIIR--

Column 10, line 34   replace "Aat1IR" with --AatIIR--

Column 11, line 18   replace "Aat1IM" with --AatIIM--

Column 11, line 18   replace "aat11M" with --aatIIM--

Column 11, line 21   replace "Eco01091" with --Eco0109I--

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu , et al.

It is certified that error appears in the above-indentified patent and that said Letters Patent is hereby corrected as shown below:

```
Column 11, line 22    replace "Eco01091" with --Eco0109I--
Column 11, line 23    replace "Eco01091" with --Eco0109I--
Column 11, line 25    replace "Eco01091" with --Eco0109I--
Column 11, line 27    replace "Eco01091" with --Eco0109I--
Column 11, line 31    replace "Eco01091" with --Eco0109I--
Column 11, line 31    replace "aatllM" with --aatIIM--
Column 11, line 34    replace "aatllR" with --aatIIR--
Column 11, line 50    replace "aatllR" with --aatIIR--
Column 11, line 51    replace "aatllM" with --aatIIM--
Column 11, line 55    replace "aatllM" with --aatIIM--
Column 11, line 60    replace "aatllR" with --aatIIR--
Column 11, line 61    replace "AatlIR" with --AatIIR--
Column 12, line 6     replace "aatllM" with --aatIIM--
Column 12, line 6     replace "aatllR" with --aatIIR--
```

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

```
Column 12, line 8     replace "aat11M" with --aatIIM--
Column 12, line 8     replace "aat11R" with --aatIIR--
Column 12, line 18    replace "aat11M" with --aatIIM--
Column 12, line 18    replace "aat11R" with --aatIIR--
Column 12, line 21    replace "aat11M" with --aatIIM--
Column 12, line 23    replace "aat11M" with --aatIIM--
Column 12, line 29    replace "aat11R" with --aatIIR--
Column 12, line 31    replace "aat11R" with --aatIIR--
Column 12, line 32    replace "aat11M" with --aatIIM--
Column 12, line 32    replace "aat11R" with --aatIIR--
Column 12, line 34    replace "aat11M" with --aatIIM--
Column 12, line 34    replace "aat11R" with --aatIIR--
Column 12, line 39    replace "Aat1IR" with --AatIIR--
Column 12, line 40    replace "Aat1IR" with --AatIIR--
```

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

Column 12, line 40      replace "[p(DNEVS" with -- (DNEV5 --

Column 12, line 48      replace "aatllR" with --aatIIR--

Column 12, line 50      replace "aatllM" with --aatIIM--

Column 12, line 57      replace "AatlIM" with --AatIIM--

Column 12, line 66      replace "aatllR" with --aatIIR--

Column 12, line 67      replace "aatllM" with --aatIIM--

Column 13, line 7       replace "aatllM" with --aatIIM--

Column 13, line 8       replace "AatlIR" with --AatIIR--

Column 13, line 19      replace "aatllM" with --aatIIM--

Column 13, line 24      replace "aatllR" with --aatIIR--

Column 13, line 33      replace "aatllR" with --aatIIR--

Column 13, line 33-34 replace "AatlIR" with --AatIIR--

Column 13, line 39      replace "aatllR" with --aatIIR--

Column 13, line 40      replace "Vent®" with --Vent®--

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

```
Column 13, line 48      replace "aat11R" with --aatIIR--
Column 13, last line 68, replace "aat11R" with --aatIIR--.
Column 14, line 30      replace "aat11M" with --aatIIM--
Column 14, line 31      replace "aat11M" with --aatIIM--
Column 14, line 33      replace "aat11M" with --aatIIM--
Column 14, line 34      replace "aat11M" with --aatIIM--
Column 14, line 41      replace "aat11M" with --aatIIM--
Column 14, line 42      replace "Vent®" with --Vent®--
Column 15, line 1       replace "aat11R" with --aatIIR--
Column 15, line 15      replace "aat11R" with --aatIIR--
Column 15, line 21      replace "aat11R" with --aatIIR--
Column 15, line 23      replace "aat11R" with --aatIIR--
Column 15, line 27      replace "aat11R" with --aatIIR--
Column 15, line 27      replace "Vent®" with --Vent®--
Column 15, line 34      replace "aat11R" with --aatIIR--
Column 15, line 39      replace "Aat1IM" with --AatIIM--
Column 15, line 48      replace "Aat1IR" with --AatIIR--
```

UNITED STATES PATENT AND TRADEMARK OFFICE
CERTIFICATE OF CORRECTION

Page 10 of 13

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

| | | |
|---|---|---|
| Column 16, line 10 | replace "Aat1IR" with | --AatIIR-- |
| Column 16, line 36 | replace "Aat1IR" with | --AatIIR-- |
| Column 16, line 37 | replace "Aat1IM" with | --AatIIM-- |
| Column 17, line 29 | replace "nla111M" with | --nlaIIIM-- |
| Column 17, line 30 | replace "nla111R" with | --nlaIIIR-- |
| Column 17, line 53 | replace "nla111M" with | --nlaIIIM-- |
| Column 17, line 56 | replace "nla111M" with | --nlaIIIM-- |
| Column 17, line 58, | replace "nla111M" with | --nlaIIIM-- |
| Column 17, line 66 | replace "Vent®" with | --Vent®-- |
| Column 17, line 66 | replace "nla111M" with | --nlaIIIM-- |
| Column 18, line 11 | replace "nla111M" with | --nlaIIIM-- |
| Column 18, line 29 | replace "nla111" with | --nlaIIIR-- |
| Column 18, line 35 | replace "nla111R" with | --nlaIIIR-- |
| Column 18, line 41 | replace "nla111R" with | --nlaIIIR-- |
| Column 18, line 42 | replace "NlaIIR" with | --NlaIIIR-- |
| Column 18, line 42 | replace "Vent®" with | --Vent®-- |
| Column 18, line 49 | replace "nla111R" with | --nlaIIIR-- |

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

```
Column 18, line 60      replace "NlalIIR" with --NlaIIIR--
Column 18, line 61      replace "NlalIIM" with --NlaIIIM--
Column 18, last line,   replace "NlalIIR" with --NlaIIIR--
Column 19, line 1       replace "NlalIIM" with --NlaIIIM--
Column 20, line 34      replace "µl5A" with --p15A--
Column 21, line 23      replace "Vent®" with --Vent®--
Column 22, line 10      replace "(CLAP)" with --(CIAP)--
Column 22, line 39      replace "alulM" with --aluIM--
Column 22, line 39      replace "alulR" with --aluIR--
Column 22, line 40      replace "alulM" with --aluIM--
Column 22, line 40      replace "alulR" with --aluIR--
Column 23, line 16      replace "alulM" with --aluIM--
Column 23, line 27      replace "alulR" with --aluIR--
Column 24, line 22      replace "alulR" with --aluIR--
Column 24, line 24      replace "Vent®" with --Vent®--
Column 24, line 44      replace "alulR" with --aluIR--
```

UNITED STATES PATENT AND TRADEMARK OFFICE
CERTIFICATE OF CORRECTION

PATENT NO. : 5,405,768
DATED : April 11, 1995
INVENTOR(S) : Shuang-yong Xu, et al.

It is certified that error appears in the above-indentified patent and that said Letters Patent is hereby corrected as shown below:

```
Column 24, line 44      replace "alulM" with --aluIM--
Column 24, line 46      replace "alulR" with --aluIR--
Column 24, line 46      replace "alulM" with --aluIM--
Column 24, line 54      replace "cl" with --cI--
Column 24, line 55      replace "cl" with --cI--
Column 24, line 60,     replace "BarnHI" with --BamHI--
Column 25, line 12      replace "alulM" with --aluIM--
Column 25, line 12      replace "alulR" with --aluIR--
Column 26, line 33      replace "alulM" with --aluIM--
Column 26, line 34-35   replace "µl5A" with --p15A--
Column 26, line 56      replace "alulM" with --aluIM--
Column 27, line 13      replace "alulM" with --aluIM--
Column 27, line 63      replace "alulR" with --aluIR--
Column 28, line 31      replace "alulR" with --aluIR--
Column 28, line 32      replace --Vent®-- with --Vent®--
Column 28, line 44      replace "alulR" with --aluIR--
Column 28, line 45      replace "BarnHI" with --BamHI--
```

UNITED STATES PATENT AND TRADEMARK OFFICE
CERTIFICATE OF CORRECTION

PATENT NO.  : 5,405,768
DATED       : April 11, 1995
INVENTOR(S) : Shuang-yong Xu, et al.

It is certified that error appears in the above-indentified patent and that said Letters Patent is hereby corrected as shown below:

Column 29, line 26     replace "alulR" with --aluIR--

Column 29, line 27     replace "alulR" with --aluIR--

Column 31, line 41     replace "2-mercaptoethanol" with --ß-mercaptoethanol--

Column 31, line 48     replace "2-mercaptoethanol" with --ß-mercaptoethanol--

Column 31, line 53     replace "2-mercaptoethanol" with --ß-mercaptoethanol--

Column 32, line 16     replace "2-mercaptoethanol" with --ß-mercaptoethanol--

Column 45, line 18,    replace "AatlIR" with --AatIIR--

Signed and Sealed this

Twelfth Day of September, 1995

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 33 base pairs
( B ) TYPE: nucleic acid
( C ) STRANDEDNESS: unknown
( D ) TOPOLOGY: unknown ( x i ) SEQUENCE DESCRIPTION: SEQ ID NO:1:

CGGGATCCGG AGGAATAAAA TGACCGCTCG TCC 33

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:2:

CCTTAACTGC AGTCATTTGT TGATATCCAG AG 32

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:3:

CTGAATTCGG AGGTTTAAAA TATGAACCCA GACGAAGTAT TTTCA 45

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:4:

TCGAGGGTCG ACTTTAGGAT TCTGATTGTG GGA 33

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:5:

CAACATATGA ATCCAGACGA AGTATTTTCA 30

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:6:

TCGAGGGTCG ACTTTAGGAT TCTGATTGTG GGA 33

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:7:

CGGGATCCGG AGGTTAATTA AATGAACTAC ATCGGCTCCA AACTA 45

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:8:

```
CAAGTCGACT TAAAAGGTCT TTTCTAAAAT ATG                     33
```

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:9:

```
TTGCATATGA AAATCACAAA AACAGAACTA                         30
```

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:10:

```
CGAGTCGACT CATCCGTTAT CTTCTTCATA TAA                     33
```

( 2 ) INFORMATION FOR SEQ ID NO:11:

( i ) SEQUENCE CHARACTERISTICS:
        ( A ) LENGTH: 996 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 1..993

( x i ) SEQUENCE DESCRIPTION: SEQ ID NO:11:

```
ATG ACC GCT CGT CCG CAA GAA AAG CAA ACA AAA CGC AAA TCA AAT CAA    48
Met Thr Ala Arg Pro Gln Glu Lys Gln Thr Lys Arg Lys Ser Asn Gln
 1               5                  10                  15

AAC TCA TGG AAG AGT AAT TTA GAA GAA AGC ATA TCT TCA ACG TGG GAA    96
Asn Ser Trp Lys Ser Asn Leu Glu Glu Ser Ile Ser Ser Thr Trp Glu
             20                  25                  30

GAT ATT AGA GAA ATT GGT GAT CAG CGG CGA TCA CAT CTT TCA AAT CGC   144
Asp Ile Arg Glu Ile Gly Asp Gln Arg Arg Ser His Leu Ser Asn Arg
         35                  40                  45

ACA ACC TAC GTT CTT GAT GAT GCA ATT CAT TTC TTA TCA GAG CTT CCT   192
Thr Thr Tyr Val Leu Asp Asp Ala Ile His Phe Leu Ser Glu Leu Pro
     50                  55                  60

CCA AAC TCT ATC CAT GCT GTT GTT ACC GAT CCT CCG TAT GGA GTC ATT   240
Pro Asn Ser Ile His Ala Val Val Thr Asp Pro Pro Tyr Gly Val Ile
 65                  70                  75                  80

GAG TAT GAA GAC AAA CAC CAC CAG AAA TTG CGC TCT GGG CGG GGC GGG   288
Glu Tyr Glu Asp Lys His His Gln Lys Leu Arg Ser Gly Arg Gly Gly
                 85                  90                  95

GTC TGG CGA ATT CCT CCT TCA TTT GAC GGT GTG AAA CGT AGC CCT CTC   336
Val Trp Arg Ile Pro Pro Ser Phe Asp Gly Val Lys Arg Ser Pro Leu
            100                 105                 110
```

| | | | | | | | | | | | | | | | | |
|---|---|---|---|---|---|---|---|---|---|---|---|---|---|---|---|---|
| CCG | CGC | TTC | ACC | GTG | CTT | TCT | GAA | GAT | GAA | TTA | AAC | AGA | TTA | AGC | AGC | 384 |
| Pro | Arg | Phe | Thr | Val | Leu | Ser | Glu | Asp | Glu | Leu | Asn | Arg | Leu | Ser | Ser | |
| | 115 | | | | | 120 | | | | | 125 | | | | | |
| TTT | TTT | TCT | GCT | TTA | GCC | TAC | GGT | TTA | CAC | CGC | GCC | CTT | GTT | CCT | GGC | 432 |
| Phe | Phe | Ser | Ala | Leu | Ala | Tyr | Gly | Leu | His | Arg | Ala | Leu | Val | Pro | Gly | |
| | 130 | | | | 135 | | | | | 140 | | | | | | |
| GGC | CAT | GTT | TTC | ATG | GCC | GCC | AAC | CCT | TTG | CTA | TCC | TCA | ATG | GTG | TTC | 480 |
| Gly | His | Val | Phe | Met | Ala | Ala | Asn | Pro | Leu | Leu | Ser | Ser | Met | Val | Phe | |
| 145 | | | | | 150 | | | | | 155 | | | | | 160 | |
| CAT | GCT | TTC | CAG | ACC | GCT | GGT | TTT | GAG | AAA | CGA | GGT | GAA | GTT | ATT | CGG | 528 |
| His | Ala | Phe | Gln | Thr | Ala | Gly | Phe | Glu | Lys | Arg | Gly | Glu | Val | Ile | Arg | |
| | | | | 165 | | | | | 170 | | | | | 175 | | |
| TTA | GTA | CAA | ACC | CTG | CGC | GGC | GGT | GAC | CGA | CCA | AAA | GGA | GCA | GAG | AAA | 576 |
| Leu | Val | Gln | Thr | Leu | Arg | Gly | Gly | Asp | Arg | Pro | Lys | Gly | Ala | Glu | Lys | |
| | | | 180 | | | | | 185 | | | | | 190 | | | |
| GAG | TTT | TCC | GAC | GTC | TCC | ATG | ATG | GCT | CGA | AGC | TGT | TGG | GAA | CCA | TGG | 624 |
| Glu | Phe | Ser | Asp | Val | Ser | Met | Met | Ala | Arg | Ser | Cys | Trp | Glu | Pro | Trp | |
| | | 195 | | | | | 200 | | | | | 205 | | | | |
| GGC | ATG | TTC | CGT | AAA | CCG | TTC | AGT | GGT | CCT | GCA | TCC | ACC | AAC | CTA | CGC | 672 |
| Gly | Met | Phe | Arg | Lys | Pro | Phe | Ser | Gly | Pro | Ala | Ser | Thr | Asn | Leu | Arg | |
| | 210 | | | | | 215 | | | | | 220 | | | | | |
| ACA | TGG | GGA | ACA | GGC | GGT | CTT | CGG | CGC | ATC | TCT | GAT | ACT | GAG | CCG | TTC | 720 |
| Thr | Trp | Gly | Thr | Gly | Gly | Leu | Arg | Arg | Ile | Ser | Asp | Thr | Glu | Pro | Phe | |
| 225 | | | | | 230 | | | | | 235 | | | | | 240 | |
| AAA | GAT | GTA | ATT | CTC | TGC | TCA | CCG | ACC | AGA | GGT | CGT | GAA | CGT | GAA | ATT | 768 |
| Lys | Asp | Val | Ile | Leu | Cys | Ser | Pro | Thr | Arg | Gly | Arg | Glu | Arg | Glu | Ile | |
| | | | | 245 | | | | | 250 | | | | | 255 | | |
| GCA | CCA | CAT | CCG | TCA | TTG | AAA | CCA | CAG | CGT | TTT | TTA | AGG | CAG | GTG | GTG | 816 |
| Ala | Pro | His | Pro | Ser | Leu | Lys | Pro | Gln | Arg | Phe | Leu | Arg | Gln | Val | Val | |
| | | | 260 | | | | | 265 | | | | | 270 | | | |
| CGT | GCA | GCC | TTA | CCC | CTA | GGA | ATT | GGG | ATT | ATC | TAC | GAC | CCC | TTT | GCT | 864 |
| Arg | Ala | Ala | Leu | Pro | Leu | Gly | Ile | Gly | Ile | Ile | Tyr | Asp | Pro | Phe | Ala | |
| | | 275 | | | | | 280 | | | | | 285 | | | | |
| GGT | AGC | GGT | TCC | ACG | CTC | GCA | GCA | GCA | GAA | GCC | GTT | GGC | TAT | CGT | GCT | 912 |
| Gly | Ser | Gly | Ser | Thr | Leu | Ala | Ala | Ala | Glu | Ala | Val | Gly | Tyr | Arg | Ala | |
| | 290 | | | | | 295 | | | | | 300 | | | | | |
| ATC | GGC | ACA | GAT | AGA | GAC | GCT | CAA | TAC | TTT | GGG | ATT | GGA | ACC | AAA | GCG | 960 |
| Ile | Gly | Thr | Asp | Arg | Asp | Ala | Gln | Tyr | Phe | Gly | Ile | Gly | Thr | Lys | Ala | |
| 305 | | | | 310 | | | | | 315 | | | | | 320 | | |
| TTT | TCA | TCT | CTT | TCC | ACT | CTG | GAT | ATC | AAC | AAA | TGA | | | | | 996 |
| Phe | Ser | Ser | Leu | Ser | Thr | Leu | Asp | Ile | Asn | Lys | | | | | | |
| | | | | 325 | | | | | 330 | | | | | | | |

( 2 ) INFORMATION FOR SEQ ID NO:12:

( i ) SEQUENCE CHARACTERISTICS:
        ( A ) LENGTH: 331 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Thr | Ala | Arg | Pro | Gln | Glu | Lys | Gln | Thr | Lys | Arg | Lys | Ser | Asn | Gln |
| 1 | | | | 5 | | | | | 10 | | | | | 15 | |
| Asn | Ser | Trp | Lys | Ser | Asn | Leu | Glu | Glu | Ser | Ile | Ser | Ser | Thr | Trp | Glu |
| | | | 20 | | | | | 25 | | | | | 30 | | |
| Asp | Ile | Arg | Glu | Ile | Gly | Asp | Gln | Arg | Arg | Ser | His | Leu | Ser | Asn | Arg |
| | | | 35 | | | | | 40 | | | | | 45 | | |
| Thr | Thr | Tyr | Val | Leu | Asp | Asp | Ala | Ile | His | Phe | Leu | Ser | Glu | Leu | Pro |
| | 50 | | | | | 55 | | | | | 60 | | | | |
| Pro | Asn | Ser | Ile | His | Ala | Val | Val | Thr | Asp | Pro | Pro | Tyr | Gly | Val | Ile |

|          |          |          |          | 65  |          |          |          |          | 70  |          |          |          |          | 75  |          |          |          |          | 80  |
|----------|----------|----------|----------|-----|----------|----------|----------|----------|-----|----------|----------|----------|----------|-----|----------|----------|----------|----------|-----|

Glu Tyr Glu Asp Lys His His Gln Lys Leu Arg Ser Gly Arg Gly
                    85                  90                  95

Val Trp Arg Ile Pro Pro Ser Phe Asp Gly Val Lys Arg Ser Pro Leu
                100                 105                 110

Pro Arg Phe Thr Val Leu Ser Glu Asp Glu Leu Asn Arg Leu Ser Ser
        115                 120                 125

Phe Phe Ser Ala Leu Ala Tyr Gly Leu His Arg Ala Leu Val Pro Gly
    130                 135                 140

Gly His Val Phe Met Ala Ala Asn Pro Leu Leu Ser Ser Met Val Phe
145                 150                 155                 160

His Ala Phe Gln Thr Ala Gly Phe Glu Lys Arg Gly Glu Val Ile Arg
                165                 170                 175

Leu Val Gln Thr Leu Arg Gly Gly Asp Arg Pro Lys Gly Ala Glu Lys
                180                 185                 190

Glu Phe Ser Asp Val Ser Met Met Ala Arg Ser Cys Trp Glu Pro Trp
            195                 200                 205

Gly Met Phe Arg Lys Pro Phe Ser Gly Pro Ala Ser Thr Asn Leu Arg
210                 215                 220

Thr Trp Gly Thr Gly Gly Leu Arg Arg Ile Ser Asp Thr Glu Pro Phe
225                 230                 235                 240

Lys Asp Val Ile Leu Cys Ser Pro Thr Arg Gly Arg Glu Arg Glu Ile
                245                 250                 255

Ala Pro His Pro Ser Leu Lys Pro Gln Arg Phe Leu Arg Gln Val Val
            260                 265                 270

Arg Ala Ala Leu Pro Leu Gly Ile Gly Ile Ile Tyr Asp Pro Phe Ala
        275                 280                 285

Gly Ser Gly Ser Thr Leu Ala Ala Ala Glu Ala Val Gly Tyr Arg Ala
    290                 295                 300

Ile Gly Thr Asp Arg Asp Ala Gln Tyr Phe Gly Ile Gly Thr Lys Ala
305                 310                 315                 320

Phe Ser Ser Leu Ser Thr Leu Asp Ile Asn Lys
                325                 330

( 2 ) INFORMATION FOR SEQ ID NO:13:

( i ) SEQUENCE CHARACTERISTICS:
        ( A ) LENGTH: 1038 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 1..1035

( x i ) SEQUENCE DESCRIPTION: SEQ ID NO:13:

ATG AAT CCA GAC GAA GTA TTT TCA GAC TTT CAG CGT GGT TTT TTT GGA     48
Met Asn Pro Asp Glu Val Phe Ser Asp Phe Gln Arg Gly Phe Phe Gly
 1               5                  10                  15

AGA AAA TTT ACT GCT GGC CTT CTG GTC TCA TTC ATT GAC TTA ATG TCT     96
Arg Lys Phe Thr Ala Gly Leu Leu Val Ser Phe Ile Asp Leu Met Ser
            20                  25                  30

GAA TTA GAA ACT CCA AAA CTT GGC ATT GCG GAT TTT GAT GGC TTT CTA    144
Glu Leu Glu Thr Pro Lys Leu Gly Ile Ala Asp Phe Asp Gly Phe Leu
        35                  40                  45

AAG CTA TTC CCA AGA CAA CTA AAA ACT AGC GCA GGG AAA CGC GCT AAT    192
Lys Leu Phe Pro Arg Gln Leu Lys Thr Ser Ala Gly Lys Arg Ala Asn
 50                  55                  60

ACT CTA ATT GTA GAA AAA GAA GAT GGG AAA ACT ATT TCT CTA AGA AAG    240

|     |     |     |     |     |     |     |     |     |     |     |     |     |     |     |     |     |
|---|---|---|---|---|---|---|---|---|---|---|---|---|---|---|---|---|
| Thr | Leu | Ile | Val | Glu | Lys | Glu | Asp | Gly | Lys | Thr | Ile | Ser | Leu | Arg | Lys | |
| 65 | | | | 70 | | | | | 75 | | | | | | 80 | |

| TTC | TAT | AAT | TCC | ATT | GAA | AAA | TTT | TAC | CGC | GCT | GAG | CAC | AAA | CGC | TTC | 288 |
|---|---|---|---|---|---|---|---|---|---|---|---|---|---|---|---|---|
| Phe | Tyr | Asn | Ser | Ile | Glu | Lys | Phe | Tyr | Arg | Ala | Glu | His | Lys | Arg | Phe | |
| | | | | 85 | | | | | 90 | | | | | 95 | | |

| GAT | TAT | CCC | AGC | GCG | GCT | CCC | CAT | GCG | ACC | CAA | GCG | TGG | GCT | GAT | TAT | 336 |
|---|---|---|---|---|---|---|---|---|---|---|---|---|---|---|---|---|
| Asp | Tyr | Pro | Ser | Ala | Ala | Pro | His | Ala | Thr | Gln | Ala | Trp | Ala | Asp | Tyr | |
| | | | 100 | | | | | 105 | | | | | 110 | | | |

| AAA | ACT | TGG | CTT | GAT | GCA | CTT | GTA | ACT | TTC | TCC | GAA | GAA | CAA | CTT | GGA | 384 |
|---|---|---|---|---|---|---|---|---|---|---|---|---|---|---|---|---|
| Lys | Thr | Trp | Leu | Asp | Ala | Leu | Val | Thr | Phe | Ser | Glu | Glu | Gln | Leu | Gly | |
| | | | 115 | | | | | 120 | | | | | 125 | | | |

| GAA | TTA | CGT | GGG | CGC | GTT | AAC | CAA | TTT | GTC | TTA | GAC | ACC | CTA | AAA | AGC | 432 |
|---|---|---|---|---|---|---|---|---|---|---|---|---|---|---|---|---|
| Glu | Leu | Arg | Gly | Arg | Val | Asn | Gln | Phe | Val | Leu | Asp | Thr | Leu | Lys | Ser | |
| | 130 | | | | | 135 | | | | | 140 | | | | | |

| CAA | GAA | TTT | GAT | CCA | ACT | TCG | GTA | AAA | GTA | GAA | CCT | CCA | TTA | TTT | CGC | 480 |
|---|---|---|---|---|---|---|---|---|---|---|---|---|---|---|---|---|
| Gln | Glu | Phe | Asp | Pro | Thr | Ser | Val | Lys | Val | Glu | Pro | Pro | Leu | Phe | Arg | |
| 145 | | | | | 150 | | | | | 155 | | | | | 160 | |

| ATT | CTT | CTA | GAA | AAA | TTC | GAA | ATG | ACC | GCC | CAA | AAA | GGC | GAG | CCT | ACA | 528 |
|---|---|---|---|---|---|---|---|---|---|---|---|---|---|---|---|---|
| Ile | Leu | Leu | Glu | Lys | Phe | Glu | Met | Thr | Ala | Gln | Lys | Gly | Glu | Pro | Thr | |
| | | | | 165 | | | | | 170 | | | | | 175 | | |

| GGG | GCT | TCT | TTC | CAA | GGA | ATA | GTC | TTT | GGA | TTT | CTT | CGA | GCC | GAC | AAT | 576 |
|---|---|---|---|---|---|---|---|---|---|---|---|---|---|---|---|---|
| Gly | Ala | Ser | Phe | Gln | Gly | Ile | Val | Phe | Gly | Phe | Leu | Arg | Ala | Asp | Asn | |
| | | | 180 | | | | | 185 | | | | | 190 | | | |

| CCT | CAT | CTT | CAA | ATT | GAA | ATC | GAC | AAA | GTC | CGC | ACT | GGC | TCC | AAA | CGA | 624 |
|---|---|---|---|---|---|---|---|---|---|---|---|---|---|---|---|---|
| Pro | His | Leu | Gln | Ile | Glu | Ile | Asp | Lys | Val | Arg | Thr | Gly | Ser | Lys | Arg | |
| | | 195 | | | | | 200 | | | | | 205 | | | | |

| CTG | CAG | CGC | ATC | GGT | GAT | GTC | GAT | GGA | TGG | GAA | GGA | GAA | CGA | TTA | GCT | 672 |
|---|---|---|---|---|---|---|---|---|---|---|---|---|---|---|---|---|
| Leu | Gln | Arg | Ile | Gly | Asp | Val | Asp | Gly | Trp | Glu | Gly | Glu | Arg | Leu | Ala | |
| | 210 | | | | | 215 | | | | | 220 | | | | | |

| ATC | TCC | GCT | GAA | GTA | AAA | CAA | TAT | GAA | ATA | AAT | ACT | GAA | TCA | ATA | GAT | 720 |
|---|---|---|---|---|---|---|---|---|---|---|---|---|---|---|---|---|
| Ile | Ser | Ala | Glu | Val | Lys | Gln | Tyr | Glu | Ile | Asn | Thr | Glu | Ser | Ile | Asp | |
| 225 | | | | | 230 | | | | | 235 | | | | | 240 | |

| GAC | CTT | GCT | GAT | TTT | GCC | AAC | AGG | ACT | GGT | CAG | CGT | GGC | GCG | TTG | GGG | 768 |
|---|---|---|---|---|---|---|---|---|---|---|---|---|---|---|---|---|
| Asp | Leu | Ala | Asp | Phe | Ala | Asn | Arg | Thr | Gly | Gln | Arg | Gly | Ala | Leu | Gly | |
| | | | | 245 | | | | | 250 | | | | | 255 | | |

| GTT | ATT | GCA | GCA | TTG | AGT | TTT | AGC | GAA | GAA | GCA | AAA | CCA | CTT | CTA | GAA | 816 |
|---|---|---|---|---|---|---|---|---|---|---|---|---|---|---|---|---|
| Val | Ile | Ala | Ala | Leu | Ser | Phe | Ser | Glu | Glu | Ala | Lys | Pro | Leu | Leu | Glu | |
| | | | 260 | | | | | 265 | | | | | 270 | | | |

| AAC | ATG | GGA | CTA | ATA | GCT | CTC | GAC | AAA | GAA | GGT | ATG | CTT | AAA | ATT | GTC | 864 |
|---|---|---|---|---|---|---|---|---|---|---|---|---|---|---|---|---|
| Asn | Met | Gly | Leu | Ile | Ala | Leu | Asp | Lys | Glu | Gly | Met | Leu | Lys | Ile | Val | |
| | | 275 | | | | | 280 | | | | | 285 | | | | |

| GAA | TTA | TGG | GAT | CCA | GTG | AAA | CAA | AGA | ACC | GCA | GTT | AGC | TCT | TTC | ATT | 912 |
|---|---|---|---|---|---|---|---|---|---|---|---|---|---|---|---|---|
| Glu | Leu | Trp | Asp | Pro | Val | Lys | Gln | Arg | Thr | Ala | Val | Ser | Ser | Phe | Ile | |
| | 290 | | | | | 295 | | | | | 300 | | | | | |

| TAC | TAT | GCA | ACC | CAT | GTC | GAG | AAA | AAT | TCG | AGT | TTG | AGC | GCC | CGT | CTT | 960 |
|---|---|---|---|---|---|---|---|---|---|---|---|---|---|---|---|---|
| Tyr | Tyr | Ala | Thr | His | Val | Glu | Lys | Asn | Ser | Ser | Leu | Ser | Ala | Arg | Leu | |
| 305 | | | | | 310 | | | | | 315 | | | | | 320 | |

| AAC | ATT | TTC | CTT | GAA | GCT | TCT | GCT | TCT | GAA | TGG | GCT | GAG | CAG | CGC | CAA | 1008 |
|---|---|---|---|---|---|---|---|---|---|---|---|---|---|---|---|---|
| Asn | Ile | Phe | Leu | Glu | Ala | Ser | Ala | Ser | Glu | Trp | Ala | Glu | Gln | Arg | Gln | |
| | | | | 325 | | | | | 330 | | | | | 335 | | |

| GCA | GCA | ATT | CTC | CCA | CAA | TCA | GAA | TCC | TAA | | | | | | | 1038 |
|---|---|---|---|---|---|---|---|---|---|---|---|---|---|---|---|---|
| Ala | Ala | Ile | Leu | Pro | Gln | Ser | Glu | Ser | | | | | | | | |
| | | | 340 | | | | | 345 | | | | | | | | |

( 2 ) INFORMATION FOR SEQ ID NO:14:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met | Asn | Pro | Asp | Glu | Val | Phe | Ser | Asp | Phe | Gln | Arg | Gly | Phe | Phe | Gly |
|---|---|---|---|---|---|---|---|---|---|---|---|---|---|---|---|
| 1 | | | | 5 | | | | | 10 | | | | | 15 | |

| Arg | Lys | Phe | Thr | Ala | Gly | Leu | Leu | Val | Ser | Phe | Ile | Asp | Leu | Met | Ser |
|---|---|---|---|---|---|---|---|---|---|---|---|---|---|---|---|
| | | | 20 | | | | | 25 | | | | | 30 | | |

| Glu | Leu | Glu | Thr | Pro | Lys | Leu | Gly | Ile | Ala | Asp | Phe | Asp | Gly | Phe | Leu |
|---|---|---|---|---|---|---|---|---|---|---|---|---|---|---|---|
| | | 35 | | | | | 40 | | | | | 45 | | | |

| Lys | Leu | Phe | Pro | Arg | Gln | Leu | Lys | Thr | Ser | Ala | Gly | Lys | Arg | Ala | Asn |
|---|---|---|---|---|---|---|---|---|---|---|---|---|---|---|---|
| | 50 | | | | | 55 | | | | | 60 | | | | |

| Thr | Leu | Ile | Val | Glu | Lys | Glu | Asp | Gly | Lys | Thr | Ile | Ser | Leu | Arg | Lys |
|---|---|---|---|---|---|---|---|---|---|---|---|---|---|---|---|
| 65 | | | | | 70 | | | | | 75 | | | | | 80 |

| Phe | Tyr | Asn | Ser | Ile | Glu | Lys | Phe | Tyr | Arg | Ala | Glu | His | Lys | Arg | Phe |
|---|---|---|---|---|---|---|---|---|---|---|---|---|---|---|---|
| | | | | 85 | | | | | 90 | | | | | 95 | |

| Asp | Tyr | Pro | Ser | Ala | Ala | Pro | His | Ala | Thr | Gln | Ala | Trp | Ala | Asp | Tyr |
|---|---|---|---|---|---|---|---|---|---|---|---|---|---|---|---|
| | | | 100 | | | | | 105 | | | | 110 | | | |

| Lys | Thr | Trp | Leu | Asp | Ala | Leu | Val | Thr | Phe | Ser | Glu | Glu | Gln | Leu | Gly |
|---|---|---|---|---|---|---|---|---|---|---|---|---|---|---|---|
| | | 115 | | | | | 120 | | | | | 125 | | | |

| Glu | Leu | Arg | Gly | Arg | Val | Asn | Gln | Phe | Val | Leu | Asp | Thr | Leu | Lys | Ser |
|---|---|---|---|---|---|---|---|---|---|---|---|---|---|---|---|
| | 130 | | | | | 135 | | | | | 140 | | | | |

| Gln | Glu | Phe | Asp | Pro | Thr | Ser | Val | Lys | Val | Glu | Pro | Pro | Leu | Phe | Arg |
|---|---|---|---|---|---|---|---|---|---|---|---|---|---|---|---|
| 145 | | | | | 150 | | | | | 155 | | | | | 160 |

| Ile | Leu | Leu | Glu | Lys | Phe | Glu | Met | Thr | Ala | Gln | Lys | Gly | Glu | Pro | Thr |
|---|---|---|---|---|---|---|---|---|---|---|---|---|---|---|---|
| | | | | 165 | | | | | 170 | | | | | 175 | |

| Gly | Ala | Ser | Phe | Gln | Gly | Ile | Val | Phe | Gly | Phe | Leu | Arg | Ala | Asp | Asn |
|---|---|---|---|---|---|---|---|---|---|---|---|---|---|---|---|
| | | | 180 | | | | | 185 | | | | | 190 | | |

| Pro | His | Leu | Gln | Ile | Glu | Ile | Asp | Lys | Val | Arg | Thr | Gly | Ser | Lys | Arg |
|---|---|---|---|---|---|---|---|---|---|---|---|---|---|---|---|
| | | 195 | | | | | 200 | | | | | 205 | | | |

| Leu | Gln | Arg | Ile | Gly | Asp | Val | Asp | Gly | Trp | Glu | Gly | Glu | Arg | Leu | Ala |
|---|---|---|---|---|---|---|---|---|---|---|---|---|---|---|---|
| | 210 | | | | | 215 | | | | | 220 | | | | |

| Ile | Ser | Ala | Glu | Val | Lys | Gln | Tyr | Glu | Ile | Asn | Thr | Glu | Ser | Ile | Asp |
|---|---|---|---|---|---|---|---|---|---|---|---|---|---|---|---|
| 225 | | | | | 230 | | | | | 235 | | | | | 240 |

| Asp | Leu | Ala | Asp | Phe | Ala | Asn | Arg | Thr | Gly | Gln | Arg | Gly | Ala | Leu | Gly |
|---|---|---|---|---|---|---|---|---|---|---|---|---|---|---|---|
| | | | | 245 | | | | | 250 | | | | | 255 | |

| Val | Ile | Ala | Ala | Leu | Ser | Phe | Ser | Glu | Glu | Ala | Lys | Pro | Leu | Leu | Glu |
|---|---|---|---|---|---|---|---|---|---|---|---|---|---|---|---|
| | | | 260 | | | | | 265 | | | | | 270 | | |

| Asn | Met | Gly | Leu | Ile | Ala | Leu | Asp | Lys | Glu | Gly | Met | Leu | Lys | Ile | Val |
|---|---|---|---|---|---|---|---|---|---|---|---|---|---|---|---|
| | | 275 | | | | | 280 | | | | | 285 | | | |

| Glu | Leu | Trp | Asp | Pro | Val | Lys | Gln | Arg | Thr | Ala | Val | Ser | Ser | Phe | Ile |
|---|---|---|---|---|---|---|---|---|---|---|---|---|---|---|---|
| | 290 | | | | | 295 | | | | | 300 | | | | |

| Tyr | Tyr | Ala | Thr | His | Val | Glu | Lys | Asn | Ser | Ser | Leu | Ser | Ala | Arg | Leu |
|---|---|---|---|---|---|---|---|---|---|---|---|---|---|---|---|
| 305 | | | | | 310 | | | | | 315 | | | | | 320 |

| Asn | Ile | Phe | Leu | Glu | Ala | Ser | Ala | Ser | Glu | Trp | Ala | Glu | Gln | Arg | Gln |
|---|---|---|---|---|---|---|---|---|---|---|---|---|---|---|---|
| | | | | 325 | | | | | 330 | | | | | 335 | |

| Ala | Ala | Ile | Leu | Pro | Gln | Ser | Glu | Ser |
|---|---|---|---|---|---|---|---|---|
| | | | 340 | | | | | 345 |

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:15:

```
GAACAGACCA TGGGATCAAT CGTCGTTGAC                                    30
```

( 2 ) INFORMATION FOR SEQ ID NO:16:

(i) SEQUENCE CHARACTERISTICS:
    (A) LENGTH: 36 base pairs
    (B) TYPE: nucleic acid
    (C) STRANDEDNESS: unknown
    (D) TOPOLOGY: unknown (xi) SEQUENCE DESCRIPTION: SEQ ID NO:16:

GCAATCGATC CGAATTCCTC TGAAGCTTGA CAGCTC    36